(12) United States Patent
Sasaki et al.

(10) Patent No.: US 7,326,386 B2
(45) Date of Patent: Feb. 5, 2008

(54) APPARATUS FOR EXTRACTING NUCLEIC ACID

(75) Inventors: Hidemi Sasaki, Asaka (JP); Katsuya Inana, Asaka (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 11/340,793

(22) Filed: Jan. 27, 2006

(65) Prior Publication Data
US 2006/0172642 A1 Aug. 3, 2006

(30) Foreign Application Priority Data
Jan. 31, 2005 (JP) ............................ P2005-022675
Mar. 30, 2005 (JP) ............................ P2005-098443

(51) Int. Cl.
*B01J 19/00* (2006.01)
(52) U.S. Cl. ...................... 422/130; 422/100; 422/101; 422/102; 422/104; 436/174; 436/175; 436/177; 436/178
(58) Field of Classification Search .......... 422/99–104, 422/129–131; 436/174, 175, 177, 178
See application file for complete search history.

(56) References Cited
U.S. PATENT DOCUMENTS 5,114,858 A     5/1992  Williams et al.
5,609,826 A *   3/1997  Cargill et al. .................. 422/99
5,961,925 A *  10/1999  Ruediger et al. .............. 422/99
6,054,100 A *   4/2000  Stanchfield et al. ......... 422/102
6,264,891 B1*   7/2001  Heyneker et al. .............. 422/64
6,267,930 B1*   7/2001  Ruediger et al. ............ 422/130
6,274,094 B1*   8/2001  Weller et al. ................ 422/130
6,432,366 B2*   8/2002  Ruediger et al. ........... 422/129
2003/0152974 A1 8/2003  Gauch et al.

FOREIGN PATENT DOCUMENTS

JP          2832586 B2      10/1998
WO       WO-00/07686 A1     2/2000
WO      WO-2005/037988 A2   4/2005
WO      WO-2005/093053 A1  10/2005

\* cited by examiner

*Primary Examiner*—Jill Warden
*Assistant Examiner*—Dwayne K Handy
(74) *Attorney, Agent, or Firm*—Birch, Stewart, Kolasch & Birch, LLP

(57) ABSTRACT

The apparatus for extracting nucleic acid includes a cartridge holder 61 which holds nucleic acid extraction cartridges 11, a container holder 62 which holds waste liquid containers 12 and recovering containers 13 and a container holding table 63 which holds the cartridge holder 61 and the container holder 62, the container holding table 63 is attachable to and detachable from an apparatus main body 2 with the cartridge holder 61 holding the nucleic acid extraction cartridges and the container holder 62 holding the waste liquid containers and the recovering containers held by the container holding table 63.

12 Claims, 29 Drawing Sheets

APPARATUS FOR EXTRACTING NUCLEIC ACID

BACKGROUND OF THE INVENTION

1. Field of the Invention

The present invention relates to an apparatus for extracting nucleic acid which automatically extracts nucleic acid in a sample solution using a nucleic acid extraction cartridge equipped with a filter member.

2. Description of the Related Art

As a conventional method for extracting nucleic acid, a centrifugation method, a method using magnetic nanoparticles, a method using a filter and the like are known.

For example, as an apparatus for extracting nucleic acid using a filter, a mechanism, which sets a number of filter tubes housing filters on a rack, dispenses a sample solution into the filter tubes, seals a periphery of a bottom portion of the rack with an air chamber via a seal member to decompress the inside, absorbs the sample solution through all the filter tubes from drain sides thereof at the same time to make the sample solution pass through the filters and adsorb nucleic acid contained in the sample solution to the filters, and then dispenses a washing solution and an eluate into the filter tubes, and repeats the decompressing and the absorbing to wash and elute the nucleic acid, has been proposed (see Japanese Patent Publication No. 2832586, for example).

SUMMARY OF THE INVENTION

The conventional automatically extracting apparatus as described above is suitable for the apparatus which is large-sized and analyzes a large number of specimens, however it has problems such that it is expensive and unsuitable for a case that the number of specimens and an analytical frequency are small, and that treatment efficiency is reduced.

Further, in such an apparatus, treatment is required to be performed in a short time, efficiently and so that contamination is not generated, and the apparatus is desired to be miniaturized and so on. However, Japanese Patent Publication No. 2832586 has a problem as described below.

A case occurs that when the characteristics of the sample solutions are different from each other as with whole sampled blood, in the apparatus for extracting nucleic acid having a constitution for absorbing an entire sample solution through all with filter tubes at the same time as disclosed in Japanese Patent Publication No. 2832586, once resistance of one of the filter tubes is removed after the absorption, decompressing operation to the other filter tubes becomes smaller and therefore treatment for a sample solution having a high viscosity is not completed. Increasing the decompressing capacity becomes an obstacle to miniaturization of the apparatus, it takes time until the decompressing operation owing to the large decompressing volume, further, it is difficult to detect that the liquid is entirely drained, a setting time is long, and therefore improvement in treatment efficiency is obstructed. On the other hand, in a sample solution having a small viscosity, the liquid is forcefully and swiftly drained from the filter tubes, contamination is generated owing to adhesion of bubbled splashes on the adjacent filter tubes and the rack, and therefore reduction in precision occurs.

Therefore, the applicant has completed a novel apparatus for extracting nucleic acid as a result of diligent study in order to solve the above-described problem. The apparatus for extracting nucleic acid adsorbs nucleic acid contained in a sample solution to a nucleic acid adsorptive porous membrane with a nucleic acid extraction cartridge housing the nucleic acid adsorptive porous membrane in a container thereof and a pressure generation apparatus, and then separates and purifies the nucleic acid through washing, etc.

Various microtubes may be employed as a microtube used as a recovering solution, for example, in a rubber cap type microtube, since tube main body 13 is engaged with each cap 13$g$ of rubber cap band 13$h$, however, there are defects such that engagement workability is inferior and the cap 13$g$ is likely to come off. Further, in a screw cap type microtube, a cap can be accurately equipped, however, there is a disadvantage of high cost. Therefore, a microtube with a cap 1A shown in FIG. 29A is suitable in terms of workability and cost, there exist a great number of requests for employment thereof.

However, a case occurs where trouble such that when an apparatus for inserting and erecting a microtube, into which a plurality of microtubes with a cap are inserted and erected, is set in the apparatus for automatically extracting nucleic acid, as shown in FIG. 30, the microtube with the cap 1A rotates around an axis line thereof due to, for example, the movement of the apparatus for inserting and erecting a microtube to a nucleic acid dispensing position in the apparatus for automatically extracting nucleic acid and a cap portion 13$a$ closes an opening portion 13$b$ of the adjacent microtube with the cap 1A.

In view of the above-described state, the present invention was made and it is an object of the present invention to provide an apparatus for inserting and erecting a microtube in which no injection trouble occurs to the inserted and erected microtube with the cap even though vibration, etc., is applied to the apparatus after being set in the apparatus for automatically extracting nucleic acid.

The novel apparatus for extracting nucleic acid 1, as shown in FIG. 19, includes: a holding mechanism 3 constituted by a cartridge holder 21 which holds a plurality of cartridges 11 and a container holding table 22 on which a rack 6 holding waste liquid containers 12 and recovering containers 13 is mounted; a pressurized air feeding mechanism 4 for introducing a pressurized air into the cartridge 11; and a dispensing mechanism 5 for dispensing a washing solution W and a recovering solution R into the cartridge 11.

The rack 6 mounted on the container holding table 22 is capable of moving (front and back movement) for exchange of the container in accordance with driving of an container exchanging motor (not shown), whereby waste liquid container 12 or the recovering container 13 is positioned under the cartridge 11.

The cartridge 11 is inserted from above into the cartridge holder 21, in which a plurality of holding holes 21$a$ are juxtaposed, and lower ends of projections 11$d$ (see FIG. 21) formed on both sides of a cylindrical main body 11$a$ of the cartridge 11 are engaged with and held by an engaging member (not shown) in the cartridge holder 21.

The rack 6 includes waste liquid container holding holes 6$a$ and recovering container holding holes 6$b$, which are extended in a lateral direction and parallel juxtaposed, in a top surface thereof, and a plurality of waste liquid containers 12 and recovering containers 13 are respectively inserted into the waste liquid container holding holes 6$a$ positioned at a rear side of the rack 6 and the recovering container holding holes 6$b$ positioned at a front side of the rack 6 to be held in a line. The waste liquid container holding holes 6$a$ and the recovering container holding holes 6$b$ are arranged at equal pitches and equal positions to the holding holes 21$a$ of the cartridge holder 21, so that each waste liquid container 12 or each recovering container 13 is positioned under each held cartridge 11.

Here, extraction operation of the above-described apparatus for extracting nucleic acid 1 will be concretely explained. As shown in FIG. 19, first, the waste liquid containers 12 and the recovering containers 13 are respectively set on the waste liquid container holding holes 6a and the recovering container holding holes 6b of the rack 6 taken out outside the apparatus main body 2, and the rack 6 is mounted on the container holding table 22 of the apparatus main body 2. Next, as shown in FIG. 20A, after the cartridge 11 is manually set on the holding hole 21a of the cartridge holder 21, as shown in FIG. 20B, a sample solution S subjected to dissolution treatment is injected into each cartridge 11 in order with a pipette, etc. As shown in FIG. 20C, each cartridge 11 into which the sample solution S is injected is thus arranged in a state of locating just above the corresponding waste liquid container 12, and preparation is completed. And then, when the apparatus for extracting nucleic acid 1 is operated by operation of an operation panel (not shown), a recovering solution R containing nucleic acid is recovered into the recovering container 13 from the sample solution S in accordance with a predetermined process.

As shown in FIG. 21A, the cartridge is formed as follows; a nucleic acid adsorptive porous membrane 11b is held on a bottom portion of the cylindrical main body 11a, of which an upper end is opened, a portion under the nucleic acid adsorptive porous membrane 11b of the cylindrical main body 11a is formed in a funnel-shape, a thin pipe nozzle-shaped drain portion 11c is projected and formed at a predetermined length on a lower end center portion of the cylindrical main body 11a, and the projections 11d are formed in a vertical direction on the both sides of the cylindrical main body 11a. After a sample solution, a washing solution and a recovering solution, which are described hereinafter, are respectively dispensed into the cartridge 11 from an upper opening 11e thereof, a pressurized air is introduced from the upper opening 11e, and each liquid is drained into the waste liquid container 12 or the recovering container 13 through the nucleic acid adsorptive porous membrane 11b from the drain portion 11c. Moreover, in FIG. 21A, the cylindrical main body is constituted so as to be divided into an upper portion and a lower portion and to be engaged with each other. Further, as shown in FIG. 21B, which shows a cross sectional view taken along line P-P, the upper opening 11e has a tilted surface 11f of which an inner circumference surface is cut in a tapered-shape, the tilted surface 11f is formed so as to substantially correspond to a tilted outer circumference surface of a tip of a pressuring nozzle (not shown) of the pressurized air feeding mechanism 4.

Extraction processes of the nucleic acid of the apparatus for extracting nucleic acid 1 will be explained.

The apparatus for extracting nucleic acid 1 basically performs extraction of the nucleic acid based on the extraction processes shown in FIG. 22A to 22G. First, in the process shown in FIG. 22A, the sample solution S containing the nucleic acid subjected to the dissolution treatment is inserted into the cartridge 11 positioned above the waste liquid container 12. Next, in the process shown in FIG. 22B, the pressurized air is introduced into the cartridge 11 and pressured, the sample solution S is made to pass through the nucleic acid adsorptive porous membrane 11b, the nucleic acid is adsorbed to the nucleic acid adsorptive porous membrane 11b, and a passed liquid component is drained into the waste liquid container 12.

Next, in the process shown in FIG. 22C, the washing solution W is automatically dispensed into the cartridge 11, in the process shown in FIG. 22D, the pressurized air is introduced into the cartridge 11 and pressured, the other impurities are washed and removed while the nucleic acid held by the nucleic acid adsorptive porous membrane 11b, and the passed washing solution W is drained into the waste liquid container 12. The processes in FIGS. 21C and 21D may be repeated two or more times.

Thereafter, in the process shown in FIG. 22E, the waste liquid container 12 under the cartridge 11 is exchanged for the recovering container 13, in the process shown in FIG. 22F, the recovering solution R is automatically dispensed into the cartridge 11, and in the process shown in FIG. 22G, the pressurized air is introduced into the cartridge 11 and pressured, a bonding force between the nucleic acid adsorptive porous membrane 11b and the nucleic acid is weakened, the adsorbed nucleic acid is separated, and the recovering solution R containing the nucleic acid is drained into the recovering container 13 to be recovered.

The above-described nucleic acid adsorptive porous membrane 11b of the cartridge 11 is basically a porous body through which the nucleic acid is allowed to pass, a surface thereof has a characteristic of adsorbing the nucleic acid in the sample solution by a chemically bonding force, to hold the adsorption during the washing by the washing solution, and to weaken the adsorption force of the nucleic acid during the recovery by the recovering solution to separate the nucleic acid from the surface.

However, there are problems as described below in the apparatus for extracting nucleic acid which automatically performs the above-described processes.

As shown in FIG. 20, preparation work for extracting the nucleic acid is performed in such a way that after the waste liquid containers 12 and the recovering containers 13 are respectively set on the rack 6 taken out outside the apparatus main body 2, the rack 6 is mounted on the container holding table 22 of the apparatus main body 2, and then the cartridges 11 are manually set on the cartridge holder 21 arranged in the apparatus main body 2. At this time, it is required that the cartridge 11, and the waste liquid container 12 or the recovering container 13, are arranged at a position where these correspond to each other. That is, when these are not arranged at the corresponding position, an error occurs due to a treatment between the items which do not correspond to each other, as well as the waste liquid, the washing solution W and the recovering solution R, which are drained from the cartridge 11 in the process for extracting the nucleic acid, are drained out of the waste liquid container 12 or the recovering container 13, and therefore not only can these liquids not be recovered but there is a possibility of contaminating the inside of the apparatus main body 2.

Further, the waste liquid containers 12 and the recovering containers 13 are mounted on the rack 6 taken out outside the apparatus main body 2, on the other hand, the cartridges 11 are set on the cartridge holder 21 fixed to the apparatus main body 2 and work is performed at the places distant from each other. Therefore, work with close attention to detail is requested so that these are mounted at the position where they correspond to each other, however there is a problem that work efficiency is low. Furthermore, in an extreme case, there is a possibility that the cartridge 11, and the waste liquid container 12 or the recovering container 13, are not arranged at the position where they do not correspond to each other.

The sample solution S should be injected into a predetermined cartridge so that analysis precision is improved, because contamination is generated when sample solution S is injected into the other cartridges. However, the cartridges 11 are set on the cartridge holder 21 arranged in a narrow space of the inside of the apparatus main body 2, and therefore the injecting of the sample solution S, which is the detailed work as described above, becomes difficult.

Further, during the extraction operation of the apparatus for extracting nucleic acid 1, the preparation work for a next extraction such as injection of the sample solution S, that the nucleic acid should be next extracted, to the cartridge 11 cannot be performed. Therefore, the preparation work for the next sample solution S should be begun after completion of the extraction regarding the previous sample solution S, and therefore the workability is low.

In view of the above problems, the present invention was made, and it is an object of the present invention to provide an apparatus for extracting nucleic acid capable of performing nucleic acid extraction treatment efficiently, easily and quickly, the treatment being excellent in automation properties and having a high reproducibility.

The present invention is constituted as described below.

(1) An apparatus for extracting nucleic acid that automatically performs an extraction operation in which, with use of a nucleic acid extraction cartridge equipped with a filter member, a sample solution containing nucleic acid is injected into the nucleic acid extraction cartridge and pressurized so that the nucleic acid in the sample solution is adsorbed to the filter member while a discharge passed through the filter member is recovered into a waste liquid container, a washing solution is dispensed into the nucleic acid extraction cartridge and pressurized so that an impurity in the nucleic acid extraction cartridge is removed by recovery of the washing solution and the impurity passed through the filter member into the waste liquid container, and then a recovering solution is dispensed into the nucleic acid extraction cartridge and pressurized so that the nucleic acid adsorbed to the filter member is separated to be recovered into a recovering container together with the recovering solution, the apparatus comprising:

a first structure that holds the nucleic acid extraction cartridge;

a second structure that holds the waste liquid container and the recovering container; and a third structure that holds the first structure and the second structure, wherein the third structure is attachable to and detachable from an apparatus main body in a state where the first structure holds the nucleic acid extraction cartridge; the second structure holds the waste liquid container and the recovering container; and the third structure holds the first structure and the second structure.

According to the apparatus for extracting nucleic acid, the first structure holding the nucleic acid extraction cartridges and second structure holding the waste liquid containers and the recovering containers are held by the third structure so that the first, second and third structures are collectively taken out outside the apparatus main body. Thus, it is possible to easily perform a detailed operation such as loading work of the cartridge and container or injecting work of the sample solution at hand. Further, it is possible to dispense a next sample in advance and prepare for the next extraction, thereby an operation rate of the apparatus can be improved.

(2) The apparatus for extracting nucleic acid as described in (1) above, further comprising:

a casing in which a plurality of insertion ports for a microtube with a cap used as the recovering container are juxtaposed on an upper surface of the casing; and a press-bending member, which is rotatably supported around an axis of a juxtaposition direction of the plurality of insertion ports provided on the casing, that holds a cap portion of the microtube with the cap by press-bending the cap portion projected from the casing downward, in the second structure that holds the waste liquid container and the recovering container.

In the second structure, the cap portion of the microtube with the cap inserted and erected into the insertion port of the casing is held by the press-bending member, and the second structure is set in the apparatus for automatically extracting nucleic acid, the top portion neither closes an opening portion of an adjacent tube main body nor comes into contact with a peripheral member, even though a vibration, etc., is applied to the casing. Therefore, no impediment for performance of the apparatus occurs.

(3) The apparatus for extracting nucleic acid as described in (2) above, wherein the microtube with the cap comprises:

a tube main body;

a flange portion provided on a circumferential edge of a tube opening portion;

a hinge portion that connects the cap portion with the flange portion; and a cylinder portion projected on a flange portion close contact surface of the cap portion, and inserted into the tube opening portion, and wherein the press-bending member comes into contact with the hinge portion to press-bend and hold the cap portion downward.

The press-bending member comes into contact with the hinge portion to press-bend and hold the cap portion, and therefore the press-bending member does not come into contact with the cylinder portion, etc., coming into contact with the inside of the tube main body to which filth must not adhere, and it is possible to avoid a trouble such that contamination occurs.

(4) The apparatus for extracting nucleic acid as described in (2) or (3) above, wherein a pair of cap position regulation plates that has a gap into which the cap portion can be inserted, and that regulates a position of the cap portion in a projecting direction from the casing while rotating the tube main body in advance of a press-bending of the cap portion is provided at both sides of the press-bending member.

Even though the microtube with a cap inserted and erected into the insertion port of the casing rotates in an arbitrary direction and the cap portion of the microtube closes the opening portion of the adjacent microtube, the pair of cap position regulation plates provided at the both sides of the press-bending member comes into contact with the side of the hinge portion by rotation of the press-bending member, and makes the cap portion project from the casing while rotating the tube main body along with the rotation of the press-bending member, thereby arranging the microtube with the cap in the gap therebetween. When the press-bending member is further rotated in this state, the press-bending member press-bends and holds the hinge portion downward.

(5) The apparatus for extracting nucleic acid as described in any of (2) to (4) above, wherein a locking mechanism that releasably holds the press-bending member press-bending the cap portion to the casing is provided over the press-bending member and the casing.

The press-bending member after press-bending of the cap portion is held on the casing via the locking mechanism, the cap portion and the tube main body are immovable to be held on the casing.

(6) The apparatus for extracting nucleic acid as described in (1) above, wherein when the first and second structures are held by the third structure, the nucleic acid extraction cartridge held by the first structure is arranged opposite to the waste liquid container held by the second structure.

According to the apparatus for extracting nucleic acid, the nucleic acid extraction cartridges held by the first structure are arranged opposite the waste liquid containers held by the second structure, and the mutual positional relationship in an initial state that the first and second structures are held by the third structure corresponds to a setting position in an initial treatment in the whole nucleic acid extraction treatment, and thus the nucleic acid extraction treatment is smoothly performed and tact-up is realized.

(7) The apparatus for extracting nucleic acid as described in (6) above, further comprising:

a movement operation member that relatively moves the second structure to the first structure, and that arranges either the waste liquid container or the recovering container under the nucleic acid extraction cartridge.

According to the apparatus for extracting nucleic acid, it is possible to arrange the waste liquid container or the recovering container under the nucleic acid extraction cartridge by driving of the moving means to automatically perform the nucleic acid extraction treatment.

(8) The apparatus for extracting nucleic acid as described in (6) or (7) above, wherein a plurality of combinations of the nucleic acid extraction cartridge and the waste liquid container and a plurality of combinations of the nucleic acid extraction cartridge and the recovering container are provided.

According to the apparatus for extracting nucleic acid, the combinations of the nucleic acid extraction cartridge and the waste liquid container corresponding to each other or the combinations of the nucleic acid extraction cartridge and the recovering container corresponding to each other for performing a series of the nucleic acid extraction treatments are arranged. Thus, the loading work of the cartridge and container, the injecting work of the sample solution or the like is not performed for the other combinations by mistake, and the work can be reliably performed.

(9) The apparatus for extracting nucleic acid as described in any of (6) to (8) above, further comprising a pair of gripping members on both sides of the third structure.

According to the apparatus for extracting nucleic acid, owing to equipment of the pair of gripping members, the first, second and third structure can be stably supported regardless of the operator's dominant arm, and practicability is improved.

(10) The apparatus for extracting nucleic acid as described in any of (6) to (9) above, further comprising a concave portion that caves into a rear side from a front side of the apparatus main body at least at the front side of the apparatus main body near an equipped position of the third structure to the apparatus main body in order to ensure side spaces of the third structure.

According to the apparatus for extracting nucleic acid, the side spaces of the third structure are ensured with the concave portions provided at the front sides of the apparatus main body, and therefore attachment/detachment operation of the third structure to/from the apparatus main body can be easily performed without interference of the apparatus main body side, and the workability is improved.

(11) The apparatus for extracting nucleic acid as described in any of (6) to (10) above, further comprising projections that regulate an insertion direction of the second structure to a specific direction on a way of an insertion passage, through which the second structure is inserted into an inside of the third structure when the second structure is held by the third structure.

According to the apparatus for extracting nucleic acid, with the insertion direction regulating means, it is possible to prevent the second structure from inserting into the third structure from an incorrect direction and to avoid a malfunction. Accordingly, it is possible to always accurately and reliably perform the nucleic acid extraction treatment.

(12) The apparatus for extracting nucleic acid as described in (11) above, wherein the projections comprise: a first projection projected on one side of an inner side wall of the insertion passage of the third structure; and a second projection projected on an outer side wall surface of the second structure facing an inner side wall of the third structure opposed to the first projection when the second structure is inserted into an inner side of the third structure in the specific direction, and wherein the first projection and the second projection do not interfere with each other when the second structure is inserted into the specific direction, and the first projection and the second projection interfere with each other so that an insertion operation is regulated when the second structure is inserted into an opposite direction of the specific direction.

According to the apparatus for extracting nucleic acid, although a constitution thereof is simple, it is possible to reliably prevent insertion from the incorrect direction owing to the provided first and second projections.

DETAILED DESCRIPTION OF THE INVENTION

Preferred embodiments of an apparatus for extracting nucleic acid according to the present invention will be explained in detail below.

Figure 1:
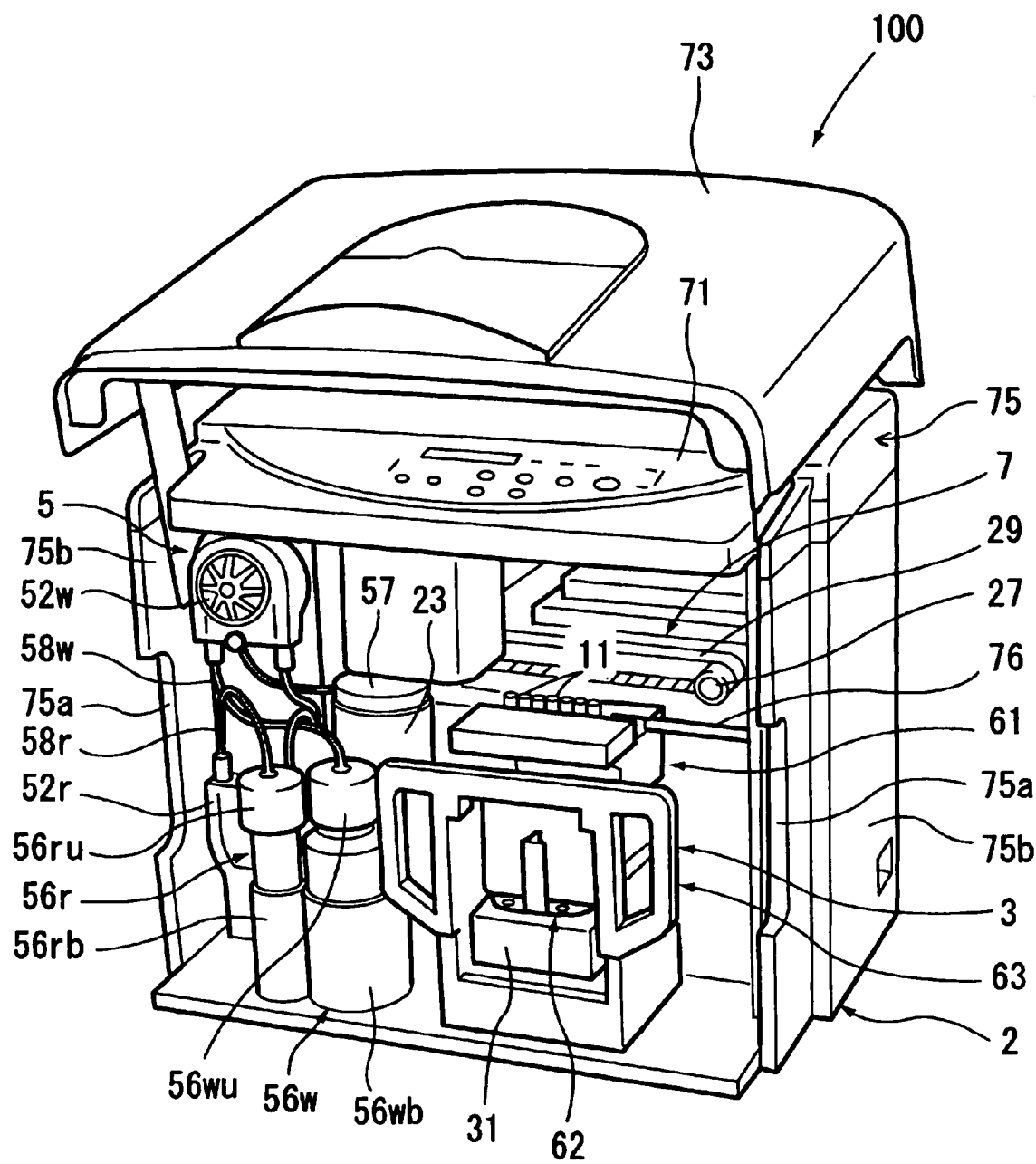
FIG. 1 is a perspective view showing a state that a front cover of an apparatus for extracting nucleic acid according to an embodiment is opened.
Figure 2:
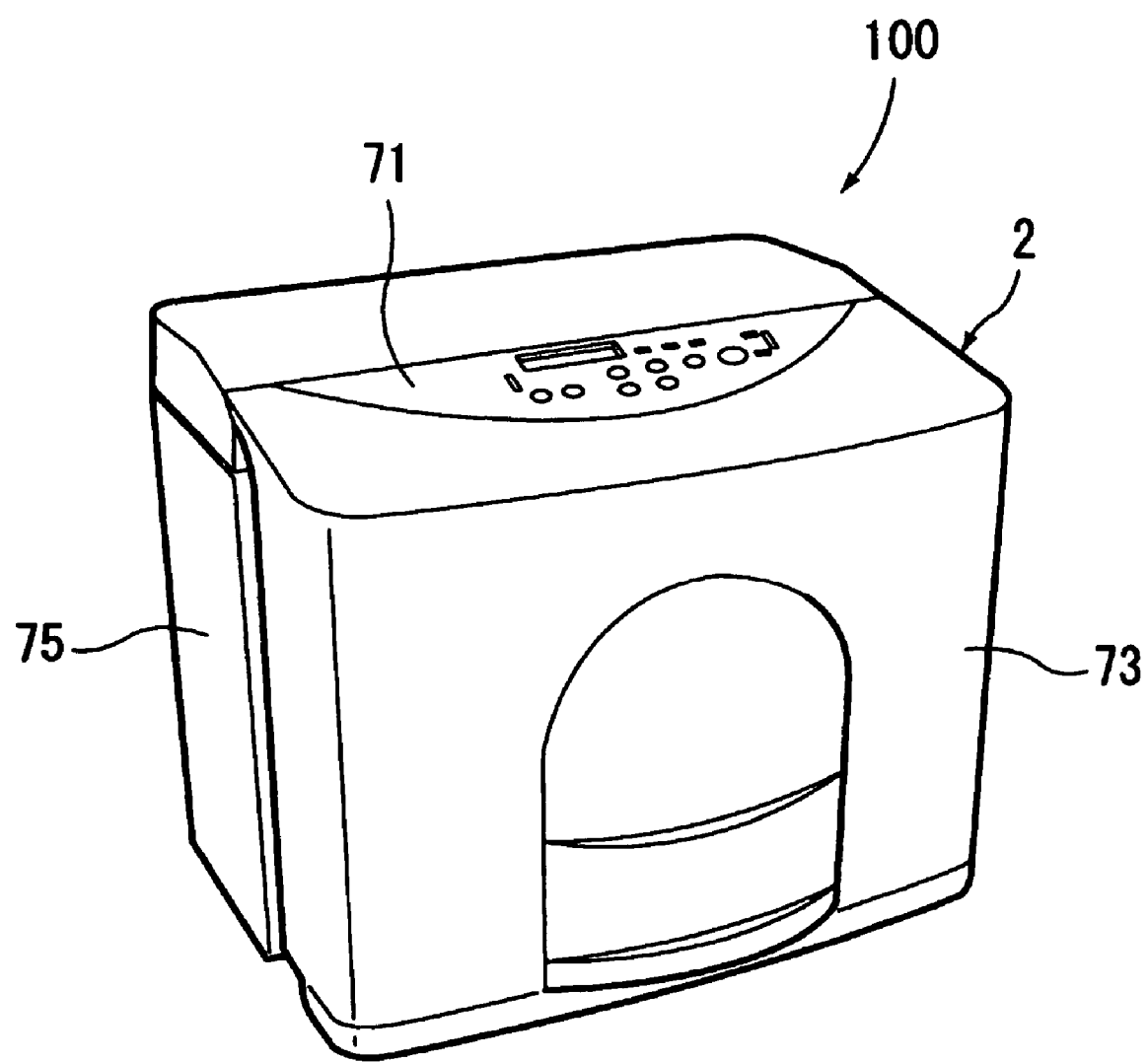
FIG. 2 is an external perspective view of the apparatus for extracting nucleic acid of which a front cover is closed.
Figure 3:
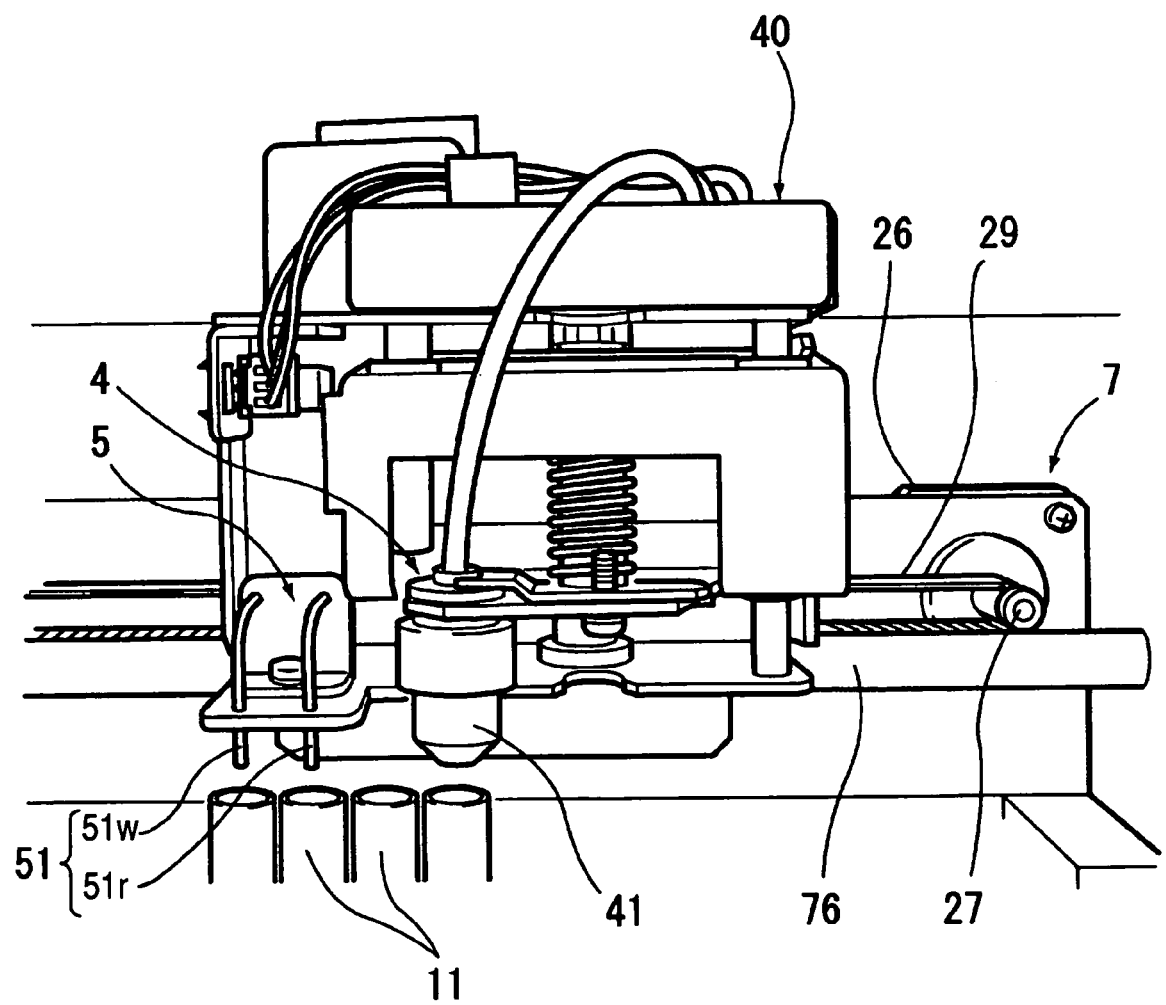
FIG. 3 is a schematic constitution view of a moving head of the apparatus for extracting nucleic acid.
Figure 4:
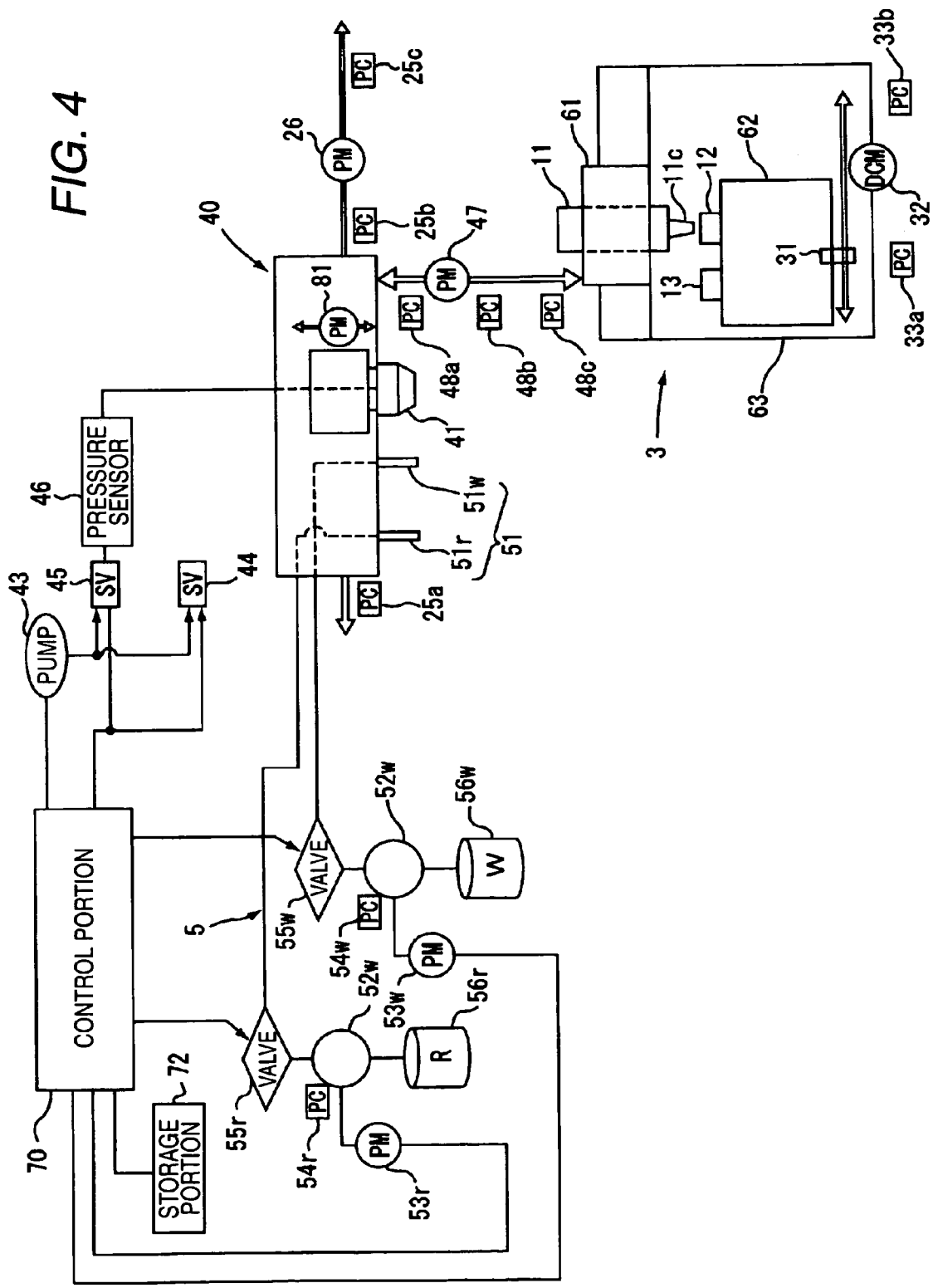
FIG. 4 is a schematic block constitution diagram of the apparatus for extracting nucleic acid.
Figure 5:
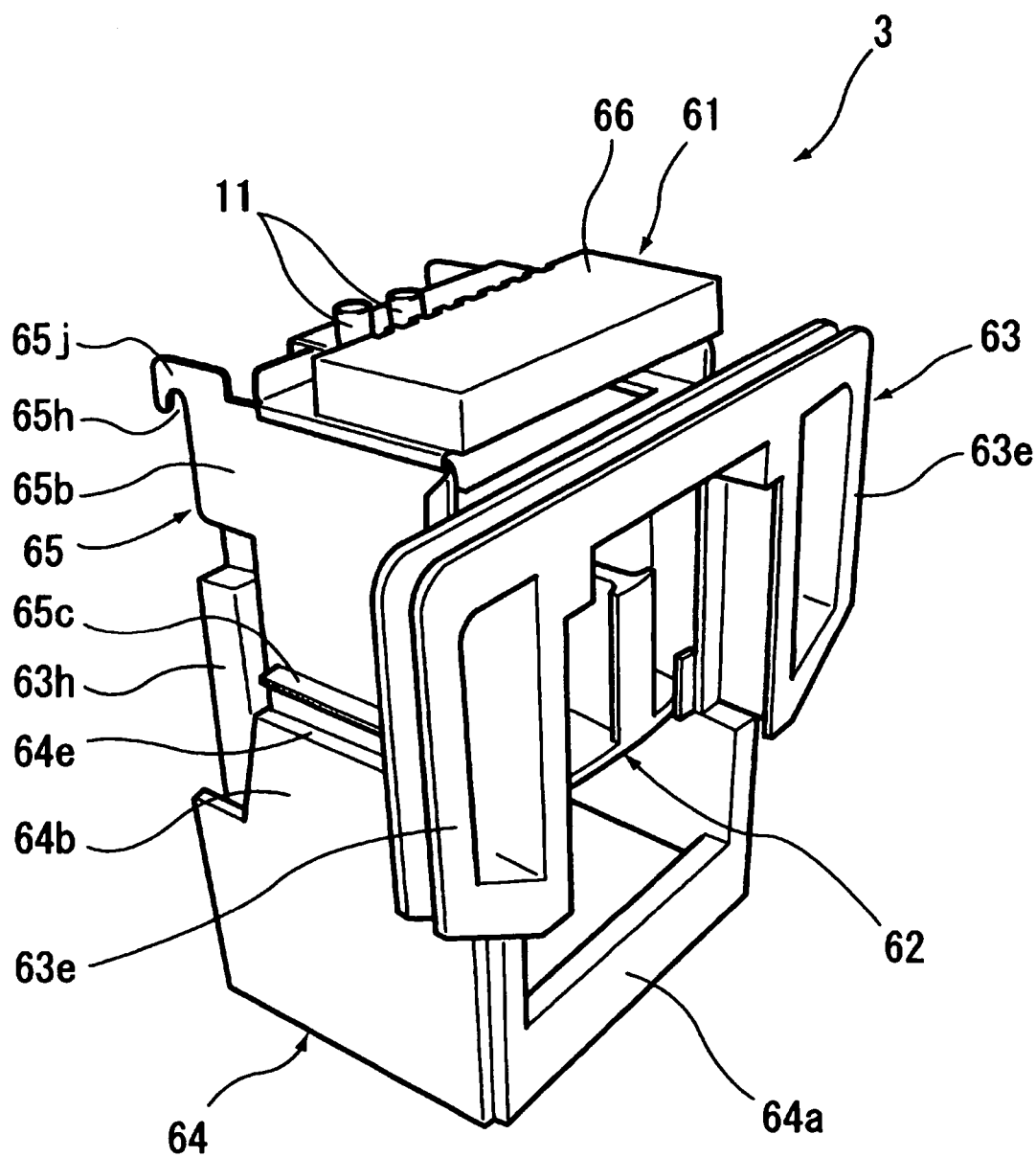
FIG. 5 is a perspective view showing a state that a cartridge holder, a container holder and a container holding table integrally assembled as a holding mechanism are mounted on a mounting table.
Figure 6:
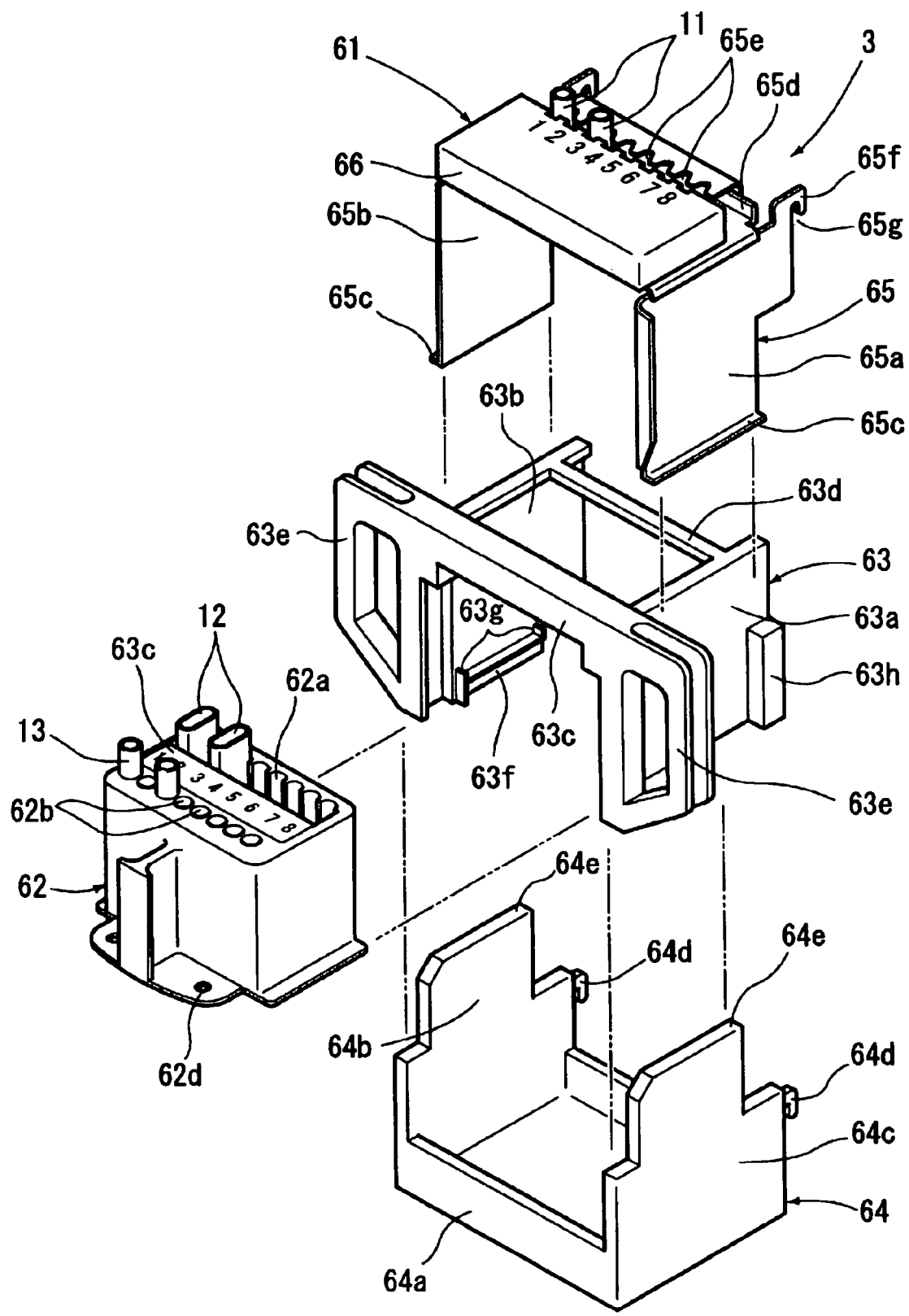
FIG. 6 is a perspective view of the cartridge holder, the container holder, the container holding table and the mounting table.

FIG. 1 is a perspective view showing a state that a front cover of an embodiment of an apparatus for extracting nucleic acid according to an embodiment is opened, FIG. 2 is an external perspective view of the apparatus for extracting nucleic acid in a state that the front cover is closed, FIG. 3 is a schematic constitutional view of a moving head of the apparatus for extracting nucleic acid, FIG. 4 is a schematic block constitutional diagram of the apparatus for extracting nucleic acid, FIG. 5 is a perspective view of a holding mechanism, and FIG. 6 is an exploded perspective view of the holding mechanism.

The apparatus for extracting nucleic acid 100 is constituted so as to include: a holding mechanism 3 for arranging and holding a plurality of nucleic acid extraction cartridges 11 housing a filter member in a container (simply referred as to "cartridge" hereinafter), waste liquid containers 12 housing a waste liquid (see FIG. 6) and recovering containers 13 housing a recovering solution containing the nucleic acid (see FIG. 6) respectively; a pressurized air feeding mechanism 4 for introducing a pressurized air into the cartridge 11 via a single pressuring nozzle 41 (see FIG. 3); a dispensing mechanism 5 having a dispensing nozzle 51 which dispenses the washing solution and recovering solution into the cartridge 11 (see FIG. 3); and a moving mechanism 7 for relatively moving the pressuring nozzle 41 of the pressurized air feeding mechanism 4 to the holding mechanism 3. A nucleic acid adsorptive porous body (nucleic acid adsorptive porous membrane in this embodiment) is employed as the filter member.

Further, the apparatus for extracting nucleic acid 100 performs steps of: (1) making a sample solution containing the nucleic acid pass through the nucleic acid adsorptive porous membrane to adsorb the nucleic acid to the porous membrane; (2) washing the nucleic acid adsorptive porous membrane with the nucleic acid adsorbed; and (3) making the recovering solution pass through the nucleic acid adsorptive porous membrane to separate the nucleic acid from the porous membrane, in this order.

Figure 21A:
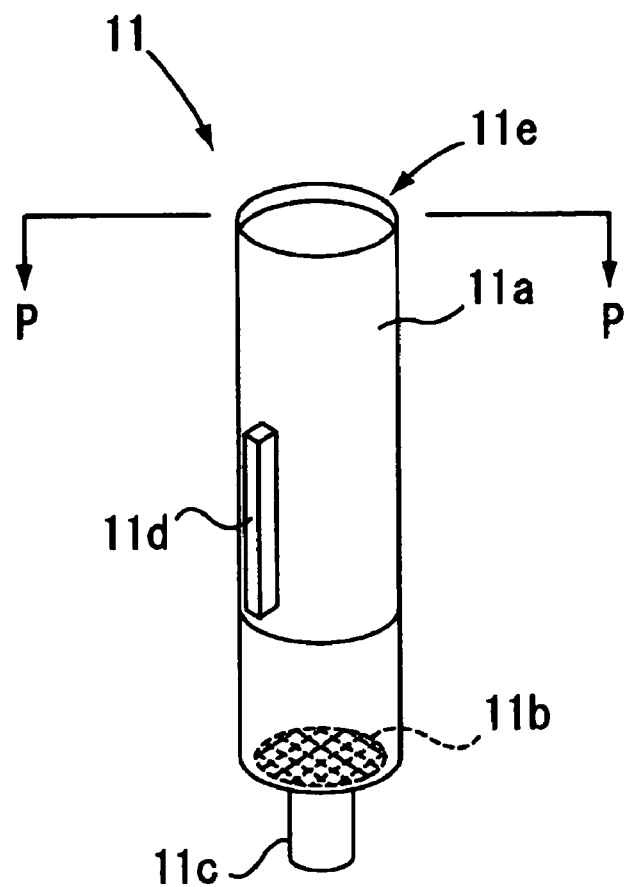
FIG. 21A is a perspective view.
Figure 21B:
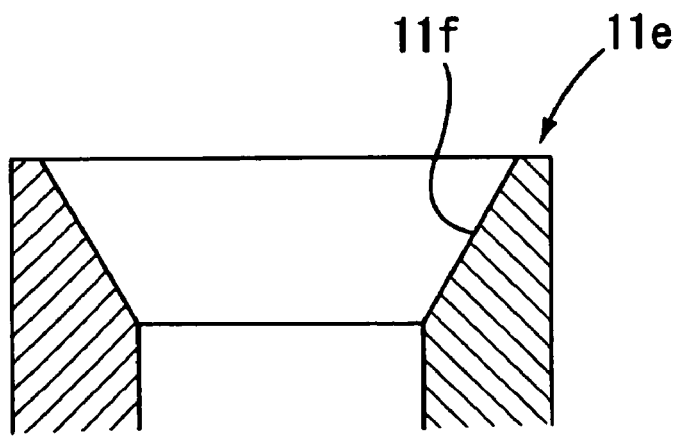
FIG. 21B is a cross sectional view taken along line P-P.
Figure 22D:
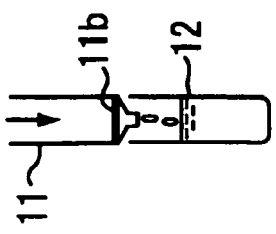
FIG. 22A to 22E are process views of extraction operation.
Figure 22C:
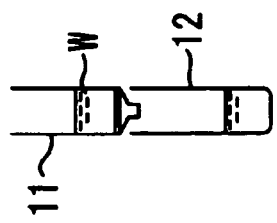
Figure 22B:
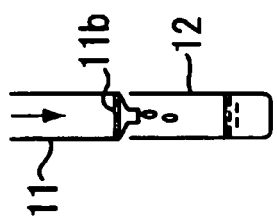
Figure 22A:
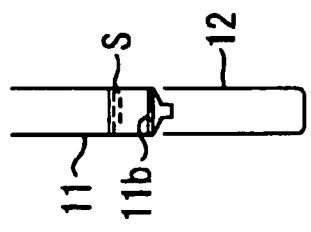
Figure 22G:
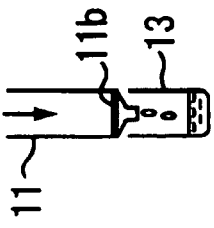
Figure 22F:
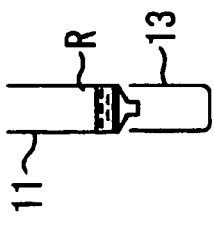
Figure 22E:
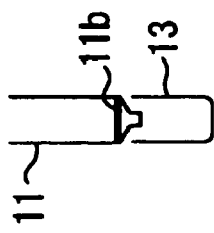

Moreover, cartridges 11 similar to the cartridge previously explained in FIG. 21 are used for the apparatus for extracting nucleic acid 100.

An apparatus main body 2 of the apparatus for extracting nucleic acid 100 includes the holding mechanism 3, the pressurized air feeding mechanism 4 for introducing a pressurized air into the cartridge 11 and the dispensing mechanism 5 for dispensing the washing solution W and the recovering solution R into the cartridge 11, as shown in FIG. 1 to 4.

The apparatus main body 2 includes a case-shaped main body portion 75 which houses the moving mechanism 7, etc., in addition to the holding mechanism 3, the pressured air feeding mechanism 4 and the dispensing mechanism 5, and which an operation panel 71 is provided on a top surface thereof and of which a front side is opened, and a front cover which covers an opened surface of the main body portion 75. Concave portions 75a, which cave into a rear side from a front side, are provided at side walls 75b of the front sides of the main body portion 75. Thus, working space is ensured at sides of a container holding table 63, when the container holding table 63 to be described later is attached to or detached from the apparatus main body 2, interference of a hand gripping the container holding table 63, etc., to the main body portion 75 is prevented, and the workability is improved.

Next, the holding mechanism 3, the pressurized air feeding mechanism 4 and the dispensing mechanism 5 will be concretely explained.

<Holding Mechanism>

The holding mechanism 3 is constituted by a cartridge holder 61 as the first structure, a container holder 62 as the second structure and the container holding table 63 as the third structure, as shown in FIG. 5 and FIG. 6. The cartridge holder 61 and the container holder 62 are respectively mounted on the container holding table 63 in a positioned state. The container holding table 63, on which the cartridge holder 61 and the container holder 62 are mounted, is further mounted on a mounting table 64.

Figure 7:
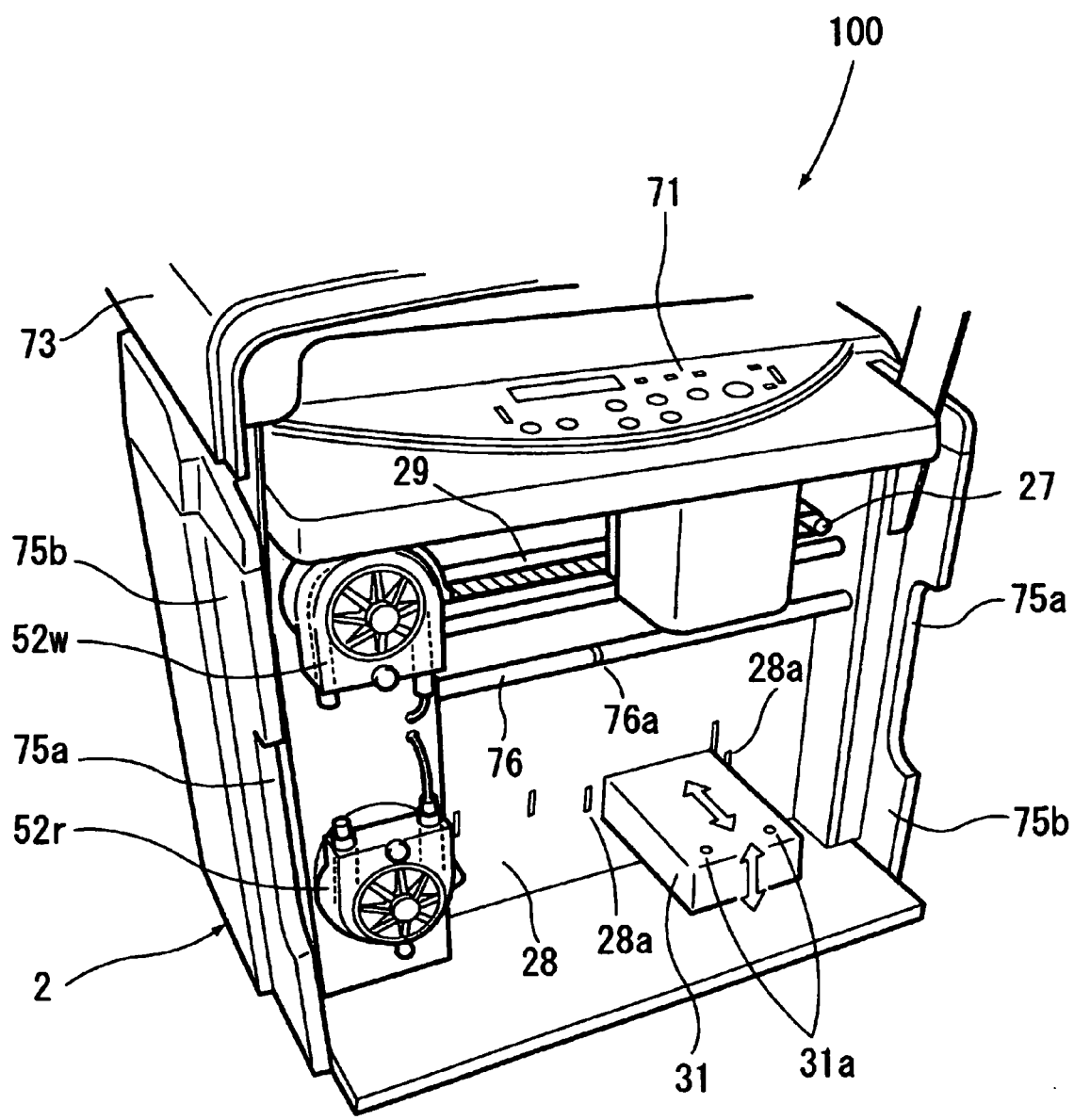
FIG. 7 is a perspective view of an apparatus main body from which the holding mechanism and liquid containers are taken out.

As shown in FIG. 7, a container exchange movement (front and back movement) of the container holder 62 is performed by a movement operation member 31, which is projected forward from a rear wall 28 of the apparatus main body 2 and movably placed in a cross direction and a vertical direction, in accordance with driving of a container exchange motor 32 (DC motor) (see FIG. 4). The recovering container 13 or the waste liquid container 12 is positioned under the cartridge 11 held by the cartridge holder 61 owing to the front and back movement. Operation of the container exchange motor 32 is controlled in accordance with detection of position sensors 33a and 33b.

The mounting table 64 is formed in such a way that both side walls 64b and 64c are projected upward from a base portion 64a formed in a substantially rectangular frame-shape. Substantially reverse U-shaped hook portions 64d are projected backward and formed on rear end upper portions of the both side walls 64b and 64c.

Figure 8B:
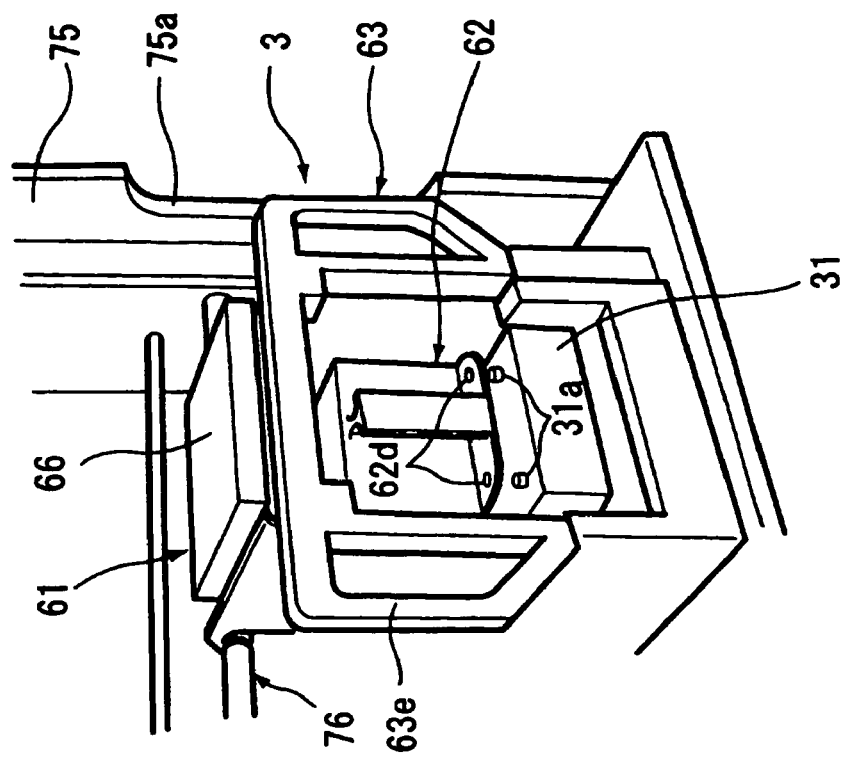
FIG. 8B is a perspective view showing a state that the holding mechanism is mounted on the mounting table.
Figure 8A:
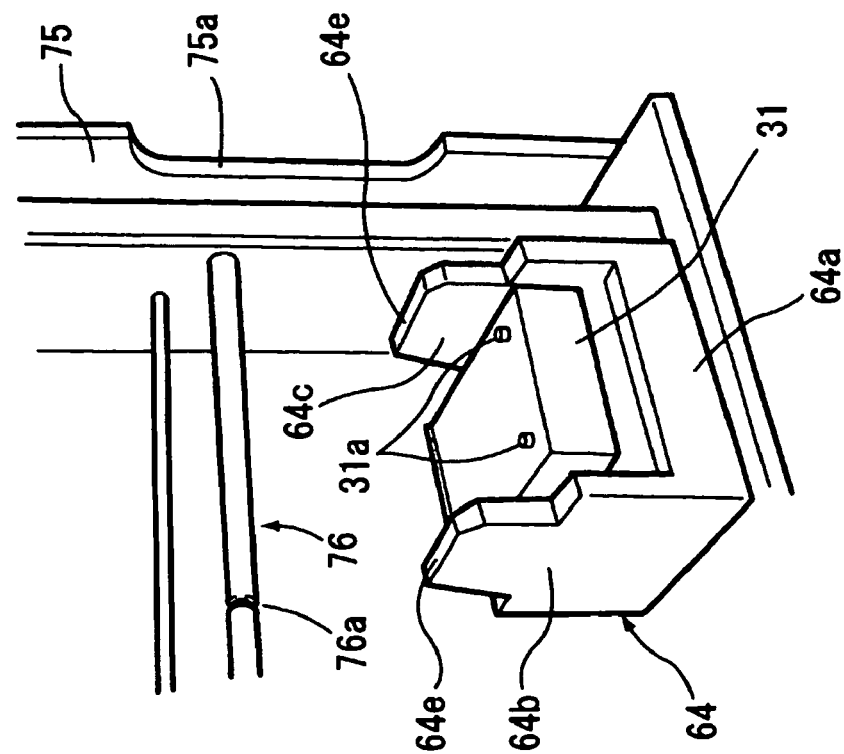
FIG. 8A is a perspective view showing a state that the mounting table is attached to the apparatus main body.

Here, FIG. 8 is a perspective view of the apparatus main body, FIG. 8A is a perspective view showing a state that the mounting table is mounted on the apparatus main body, and FIG. 8B is a perspective view showing a state that the holding mechanism is further mounted on the mounting table.

As shown in FIG. 8A, the mounting table 64 is placed in the apparatus main body 2 in such a way that: the hook portions 64d are inserted into and engaged with rectangular locking holes 28a (see FIG. 7) formed in the rear wall 28 of the apparatus main body 2 so that the base portion 64a is positioned under the movement operation member 31; and the both side walls 64b and 64c are provided at both sides of the movement operation member 31. Accordingly, the movement operation member 31 freely moves in the cross direction and the vertical direction between the both side walls 64b and 64c.

Further, as shown in FIG. 8B, the holding mechanism 3, to which the cartridge holder 61, the container holder 62 and the container holding table 63 are integrally attached, is mounted on the mounting table 64 placed in the apparatus body 2.

The cartridge holder 61 includes a table portion 65 formed by folding and bending of a stainless steel sheet, etc., in a substantial U-shape and a plate member 66, and is constituted by a structure divided into two. Lower ends of both side walls 65a and 65b of the table portion 65 are bent in a direction separating from each other to form a supporting portion 65c. Further, locking portions 65f and 65j respectively having substantially reverse U-shaped locking grooves 65g and 65h are formed at rear end upper portions of the both side walls 65a and 65b (see FIG. 5 and FIG. 6). These locking portions 65f and 65j are respectively engaged and positioned with a locking rod 76 and a notch groove 76a of the locking rod 76.

Figure 9:
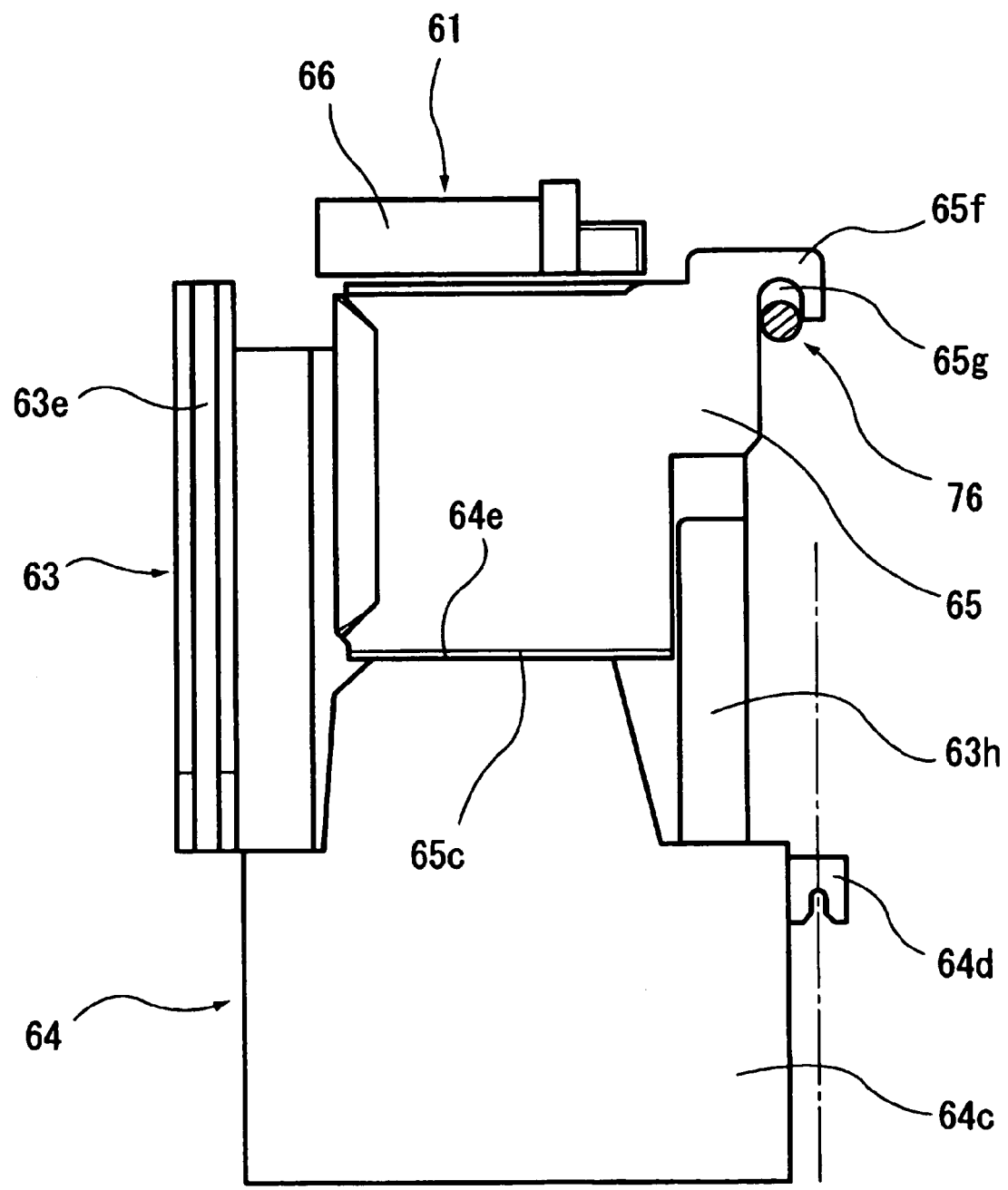
FIG. 9 is a side view showing a state that the holding mechanism is locked on a locking rod and attached to the apparatus main body.
Figure 10:
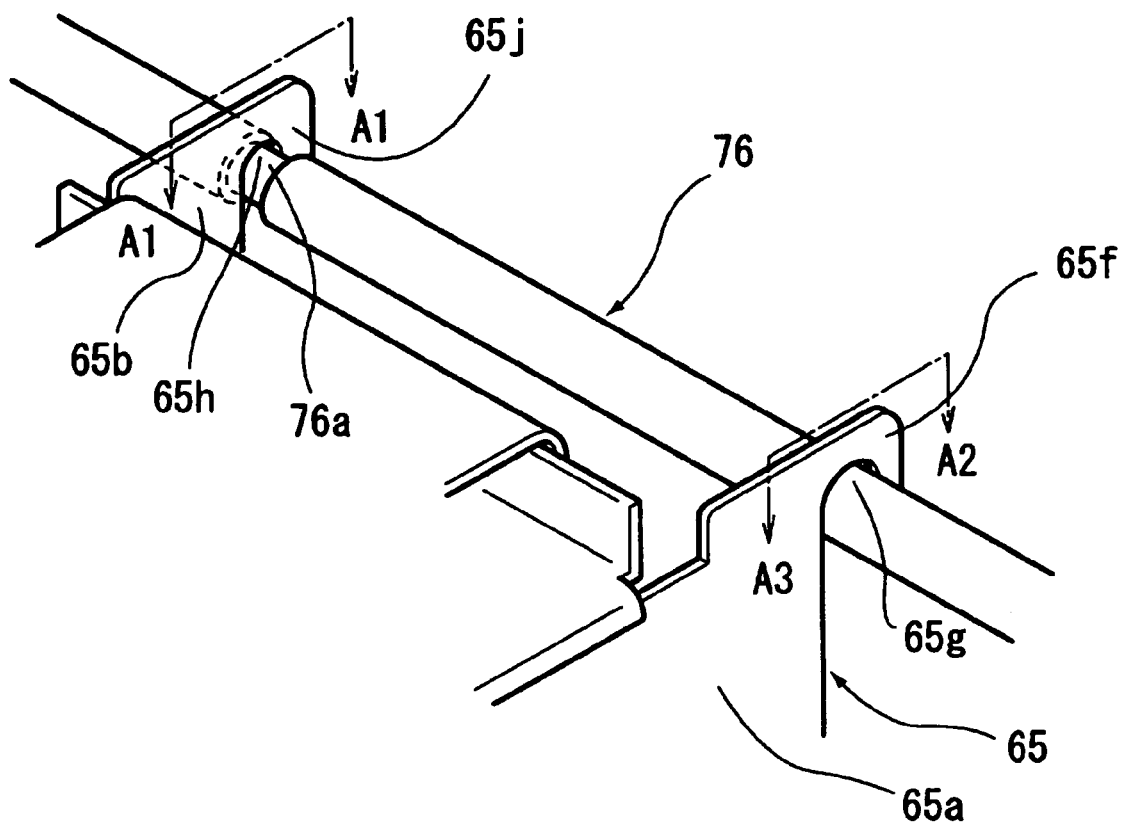
FIG. 10 is a main portion enlarged perspective view showing a state that the cartridge holder is locked on the locking rod.

Concretely, as shown in FIG. 9 to FIG. 11, the holding mechanism 3 is mounted on the mounting table 64, with the locking groove 65g engaged with an outer circumference of the locking rod 76 and the locking groove 65h engaged with the notch groove 76a of the locking rod 76. The locking groove 65h is engaged with the notch groove 76a so that the front and back movement of the cartridge holder 61, that is, the holding mechanism 3 is limited while a lateral position is regulated. At this time, a supporting portion 65c is brought into contact with upper surfaces 64e of the both side walls 64b and 64c of the mounting table 64, and thus the vertical direction position of the cartridge holder 61 is determined.

A rear end of a middle portion 65d which connects the side wall 65a with the side wall 65b is further folded and bent in a substantial inverted C-shape, and includes a plurality of V-shaped holding grooves 65e formed in the V-shape (eight places as illustrated in the embodiment).

The plate member 66 is movably constituted in a direction of separating from and coming into contact with the V-shaped holding grooves 65e of the table portion 65 and urged in a direction of approaching the V-shaped holding grooves 65e with a coil spring built therein (not shown). Further, a plurality of V-shaped holding portions (not shown) are formed at the plate member 66 at places corresponding to the V-shaped holding grooves 65e of the table portion 65, and the cartridges 11 are held between the V-shaped holding grooves 65e of the table portion 65 and the holding portions of the plate member 66 by an elastic force of the coil spring. That is, the gripping mechanism of the cartridges 11 is constituted by the V-shaped holding grooves 65e of the table portion 65, the holding portions of the plate member 66 and the coil spring.

Projections 11d of the cartridges 11, which are formed on the both sides of a cylinder main body 11a, are engaged with and held by engaging portions (not shown) of the plate member 66, and thus the cartridges 11 are held by the gripping mechanism. When the plate member 66 is moved against the elastic force of the coil spring, engagement with the projections 11d is released, and all the cartridges 11 are dropped and discarded at the same time. Further, numbers are recorded in an ascending order at positions corresponding to the holding portions of the plate member 66 respectively, and the held cartridges 11 can be easily identified.

In the container holding table 63, as shown in FIG. 6, a pair of side walls 63a and 63b are connected by ribs 63c and arranged opposite each other. The rib 63c is extended to both sides so that the pair of gripping members 63e is formed. Further, a pair of supporting ribs 63f facing each other is formed along a horizontal direction on inner wall surface lower portions of the pair of side walls 63a and 63b respectively, and the container holder 62 can be mounted on the supporting ribs 63f. Projections 63g projected upward are formed on the upper surface both ends of the supporting rib 63f respectively, the container holder 62 mounted on the supporting ribs 63f comes into contact with the projections 63g to be positioned in the cross direction. Furthermore, vertical ribs 63h are formed in vertical directions on the front of the outer wall surfaces of the pair of side walls 63a and 63b respectively. The cartridge holder 61 is mounted on the container holding table 63 in a positioned state in such a way that the both sidewalls 65a and 65b are respectively inserted between the vertical ribs 63h and the holding members 63e from above while holding the pair of side walls 63a and 63b of the container holding table 63.

The container holder 62 includes a waste liquid container holding holes 62a and a recovering container holding holes 63b, which are extended in a lateral direction and parallel juxtaposed, in a top surface thereof, and a plurality of waste liquid containers 12 and recovering containers 13 are respectively held in a line by the waste liquid container holding holes 62a positioned at a rear side of the holder 62 and the recovering container holding holes 62b positioned at a front side of the holder 62. The waste liquid container holding holes 62a and the recovering container holding holes 62b are respectively arranged at equal pitches and equal position with a gripping mechanism (V-shaped holding grooves 65e) of the cartridge holder 61, so that each waste liquid container 12 and each recovering container 13 are positioned under each held cartridge 11.

Numbers corresponding to the numbers recorded on the cartridge holder 61 respectively are recorded in an ascending order on a top surface 62c between the juxtaposed waste liquid container holding holes 62a and recovering container holding holes 62b. Thus, it is possible to identify one by one each corresponding combination of the cartridges 11 held by the cartridge holder 61 and the waste liquid containers 12 or the recovering containers 13 held by the container holder 62. A pair of positioning holes 62d is formed on a bottom surface of the container holder 62.

Moreover, it is preferable that sizes and shapes of the waste liquid container 12 and the recovering container 13 are different from each other for prevention of confusion.

As shown in FIG. 5, the cartridge holder 61 is inserted into and mounted on the container holding table 63 from above so that the both side walls 65a and 65b hold the pair of side walls 63a and 63b of the container holding table 63. Further, the container holder 62 is inserted from an opening at a front side of the container holding table 63 to be mounted on the pair of supporting ribs 63f. Thus, the cartridge holder 61, and the container holder 62 and the container holding table 63 are integrally attached, and the holding mechanism 3 is constituted. The holding mechanism 3 is mounted on the mounting table 64 placed in the apparatus main body 2, on the other hand, the supporting portions 65c of the cartridge holder 61 are brought into contact with and held by the upper surfaces 64e of the both side walls 64b and 64c of the mounting table 64.

Moreover, in a lowered position that the container holder 62 is mounted on the pair of supporting ribs 63f (see FIG. 6) as shown in FIG. 5, a lower end of the drain portion 11c of the cartridge 11 held by the cartridge holder 61 locates higher than the waste liquid container 12 and the recovering container 13 set on the container holder 62. When the container holder 62 is operated up and down by driving of an elevating-lowering motor 47 (see FIG. 4) such as a pulse motor and is moved up and down by control with detection of photo-sensors 48a to 48c, the drain portion 11c of the cartridge 11 is inserted into the waste liquid container 12 or the recovering container 13 at a predetermined amount during the elevation of the container holder 62.

<Pressurized Air Feeding Mechanism>

The pressurized air feeding mechanism 4, as shown in FIG. 4, includes: a moving head 40 as a movable body which moves up and down to the container holder 62; a single pressuring nozzle 41 placed in the moving head 40; an air pump 43 which generates the pressurized air; a relief valve 44; a switching valve 45 which is placed at the pressuring air nozzle 41 side and opens and closes an air feeding passage; a pressure sensor 46 placed at the pressuring air nozzle 41 side; and nozzle elevating/lowering means for elevating/lowering the pressuring nozzle 41. The nozzle elevating/lowering means realizes elevating/lowering operation by a nozzle elevating/lowering motor 81 such as a pulse motor and a screw-nut mechanism connected thereto. By this constitution, the pressurized air is fed into the cartridges 11 in order. The air pump 43, the relief valve 44 and the pressuring muzzle 41 respectively operated based on instructions for controlling from a control portion 70.

The moving head 40 includes: a head moving motor 26 (see FIG. 3 and FIG. 4) such as a pulse motor as moving means placed in the apparatus main body 2; a driving side pulley 27 rotationally driven by the head moving motor 26; a driven side pulley (not shown) which is rotatable and performs a tension adjustment; and a timing belt 29 suspended between the driving side pulley 27 and the driven side pulley. Moreover, the head moving motor 26 is driven by control with detection of photo-sensors 25a to 25c and moves the moving head 40 along an arrangement direction of the cartridges 11.

The pressuring nozzle 41 is placed on the moving head 40 so as to be movable in the vertical direction and urged downward, and an outer circumference surface of a lower tip of the pressuring nozzle 41 is conical-shaped. Thus, when the pressuring nozzle 41 lowers, the tip of the pressuring nozzle 41 is brought into contact with an upper opening 11e of the cartridge 11 set on the cartridge holder 61 so that a conical surface of the tip of the pressuring nozzle 41 is brought into close contact with a tilted surface 11f of the cartridge 11 cut in a tapered-shape to seal the inside of the cartridge 11. It is possible to feed the pressurized air into the cartridge 11 with no leakage under the sealing state.

The relief valve 44 is subjected to air open-operation during the exhaust of air in a passage between the air pump 43 and the switching valve 45. An air circuit is constituted in such a way that the switching valve 45 is selectively open-operated so that the pressurized air from the air pump 43 is introduced into the cartridge 11 via the pressuring nozzle 41. By the above-described constitution, an air feeding flow passage is formed between the air pump 43 and the cartridge 11.

<Dispensing Mechanism>

As shown in FIG. 1, FIG. 3, FIG. 4 and FIG. 7, the dispensing mechanism 5 includes: a washing solution dispensing nozzle 51w and a recovering solution dispensing mechanism 51r integrally mounted on the moving head 40 movable on the cartridge holder 61 in the arrangement direction of the cartridges 11; a washing solution feed pump 52w which feeds the washing solution W housed in a washing solution bottle 56w into the washing solution dispensing nozzle 51w; a recovering solution feed pump 52r which feeds the recovering solution R housed in a recovering solution bottle 56r into the recovering solution dispensing nozzle 51r; a waste liquid container 57 mounted on a waste liquid container table 23 and the like.

The moving head 40 stops above each cartridge 11 in order by the head moving motor 26 and stops above a waste liquid container 57 in a state of return to be driven and controlled so as to open a space above each cartridge 11. Workability is greatly improved by the opening of the space above each cartridge 11.

Tips of the washing solution dispensing nozzle 51w and the recovering solution dispensing nozzle 51r are bent downward, the washing solution dispensing nozzle 51w is connected to the washing solution feed pump 52w via a valve 55w, and the washing solution feed pump 52w is connected to the washing solution bottle 56w. The recovering solution dispensing nozzle 51r is connected to the recovering solution feed pump 52r via a valve 55r, and the recovering solution feed pump 52r is connected to the recovering solution bottle 56r. The washing solution bottle 56w and the recovering solution bottle 56r are respectively equipped at a front side of the apparatus main body so that operability thereof is enhanced. The washing solution feed pump 52w and the recovering solution feed pump 52r are respectively constituted by a tube pump, and are respectively driven and controlled to dispense each predetermined amount of the washing solution W and recovering solution R based on position detections of sensors 54w and 54r by pump motors 53w and 53r (pulse motors). These pump motor 53w and 53r and these valve 55w and 55r are operated based on instructions from the control portion 70.

When the washing solution W or the recovering solution R is dispensed, the valve 55w or 55r is opened, the pump motor 53w or 53r is driven, and a rotor member of the washing solution feed pump 52w or the recovering solution feed pump 52r is rotated. Thus, the washing solution W or the recovering solution R is absorbed by the washing solution feed pump 52w or the recovering solution feed pump 52r to be ejected from the washing solution dispensing nozzle 51w or the recovering solution dispensing nozzle 51r via the valve 55w or the 55r. The washing solution dispensing nozzle 51w or the recovering solution dispensing nozzle 51r is required to be moved above the cartridge 11 during the ejection. Thus, the predetermined amount of the washing solution W or the recovering solution R is dispensed into the cartridge 11.

The washing solution bottle 56w and the recovering solution bottle 56r are constituted by container main bodies 56wb and 56rb, and caps 56wu and 56ru, respectively. Thin pipe-shaped absorbing tubes 58w and 58r are placed on the caps 56wu and 56ru respectively, lower ends of the absorbing tubes 58w and 58r are opened near bottom portions of the container main bodies 56wb and 56rb respectively, and the washing solution W or the recovering solution R is absorbed in accordance with operation of the washing solution feed pump 52w or the recovering solution feed pump 52r.

Each mechanism 3 to 5 as described above is controlled by the linked control portion 70 (see FIG. 4) in accordance with input operation of an operation panel 71 placed on an upper portion of the apparatus main body 2. That is, each mechanism 3 to 5 is driven and controlled based on a program previously stored in a storage portion 72 connected to the control portion 70. Further, as shown in FIG. 1 and FIG. 2, each mechanism 3 to 5 is housed in the apparatus main body 2 by covering the front of the apparatus main body 2 with a front cover 73 provided freely to open/close the apparatus main body 2.

Next, extraction operation of the apparatus for extracting nucleic acid 100 constituted as the above-described will be concretely explained.

First, as shown in FIG. 8A, the hook portions 64d of the mounting table 64 are inserted into and engaged with the rectangular locking holes 28a (see FIG. 7) formed on the rear wall 28 of the apparatus main body 2, the base portion 64a is positioned under the movement operation member 31, the movement operation member 31 is held between the both side walls 64b and 64c, and thus the mounting table 64 is placed in the apparatus main body 2.

Figure 12A:
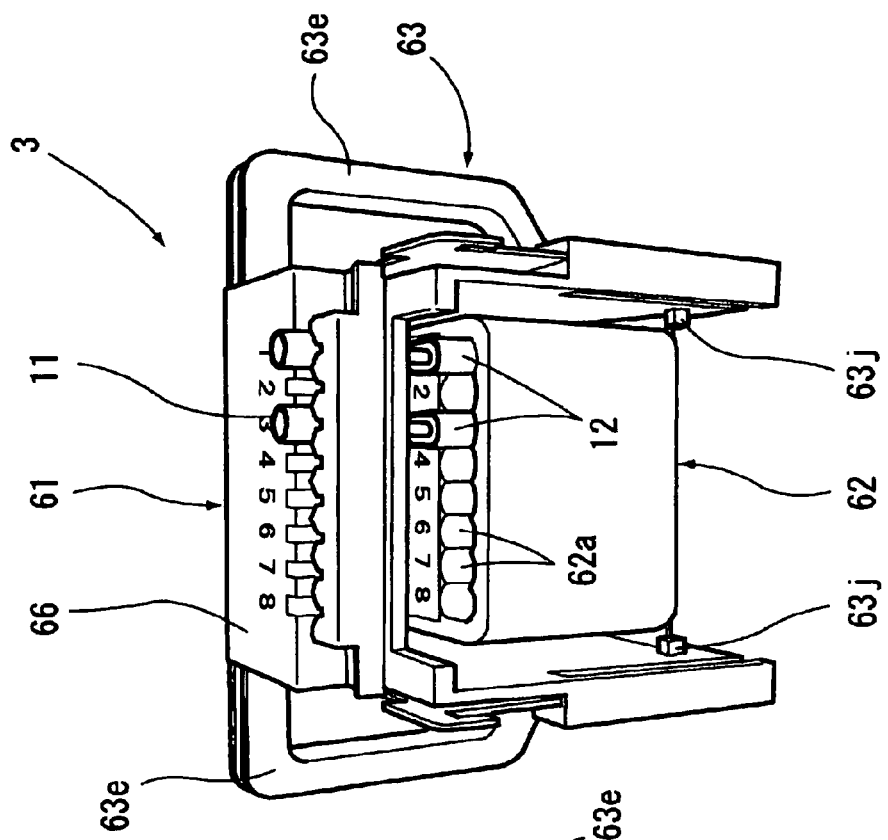
FIG. 12A is a perspective view showing a state that the container holder is inserted into the container holding table on which the cartridge holder is mounted.
Figure 12B:
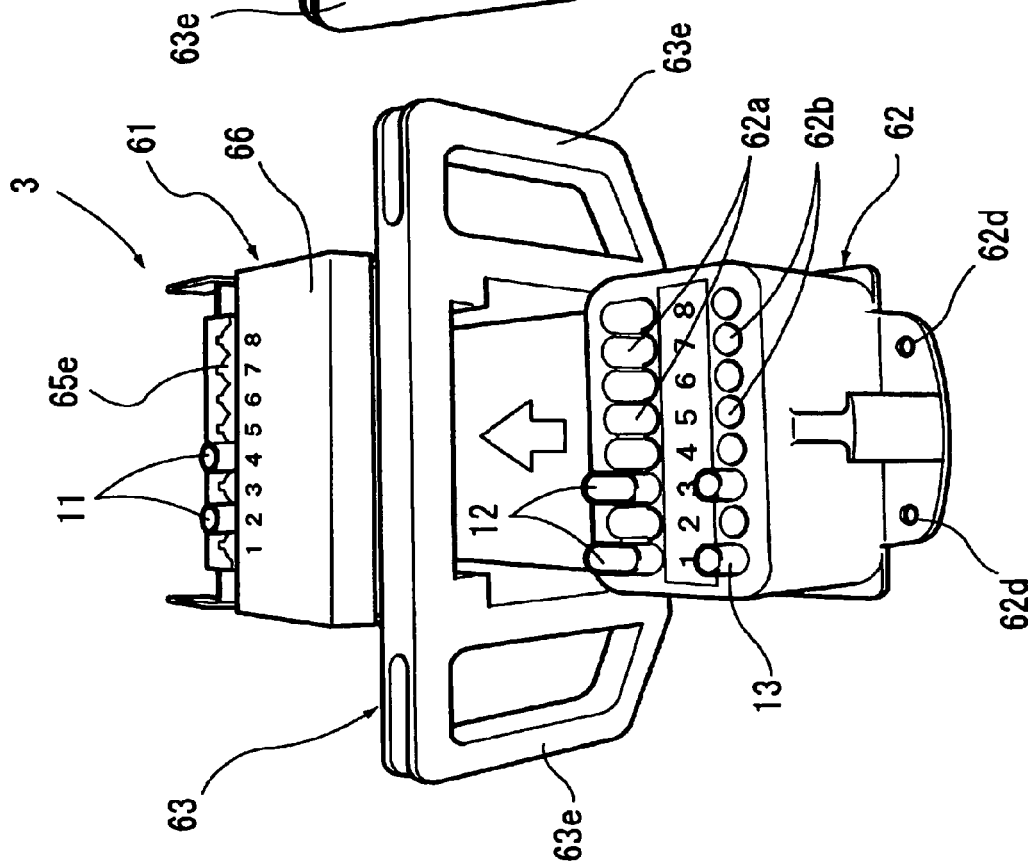
FIG. 12B is a perspective view of the holding mechanism in which the cartridge holder, the container holder and the container holding table are assembled to the container holding table.

Next, as shown in FIG. 12A, the cartridge holder 61 of the holding mechanism 3 taken out outside the apparatus main body 2 is mounted on the container holding table 63 with the cartridges 11 set on the cartridge holder 61. Here, a case that the maximum number of cartridges 11 (eight pieces in the figures) are used will be explained. The waste liquid containers 12 and the recovering containers 13 are inserted into and held by the waste liquid container holding holes 62a and the recovering container holding holes 62b of the container holder 62 respectively, the container holder 62 is inserted into the container holding table 63 from the front side opening of the table 63 to be mounted on the pair of supporting ribs 63f. As shown in FIG. 12B, the holding mechanism 3 is thus assembled with the cartridges 11 positioned above the waste liquid containers 12. In this state, the sample solution S subjected to the dissolution treatment is inserted into each cartridge 11 in order using a pipette, etc.

The preparation work described above is performed at a widely opened place such as a work table arranged outside of the apparatus main body 2 to be extremely easy and efficient in comparison with conventional apparatuses for extracting nucleic acid which perform work in narrow apparatus main bodies. Thus, during the injection of the sample solution S, generation of contamination owing to contact of the pipette or the sample solution S with the adjacent cartridges 11 is prevented.

It becomes easy to align at hand and arrange the cartridge holder 61 and the container holder 62 referring to the numbers recorded on the cartridge holder 61 and the container holder 62 so that the cartridges 11 respectively correspond to the waste liquid containers 12 or the recovering containers 13 by a constitution that the cartridge holder 61 and the container holder 62 can be taken out from the apparatus main body 2 together with the container holding table 63. Detailed operation such as loading work of each of containers 11, 12 and 13 or injection work of the sample solution S is performed in this state so that an erroneous operation such as an erroneous loading of the cartridges 11, the waste liquid containers 12 and the recovering containers 13 or injection of the sample solution S into a different container can be prevented.

Figure 11A:
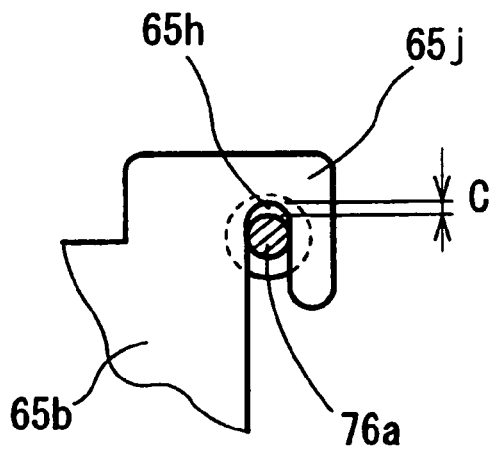
FIG. 11A is a vertical cross sectional view taken along line A1-A1 in FIG. 10.
Figure 11B:
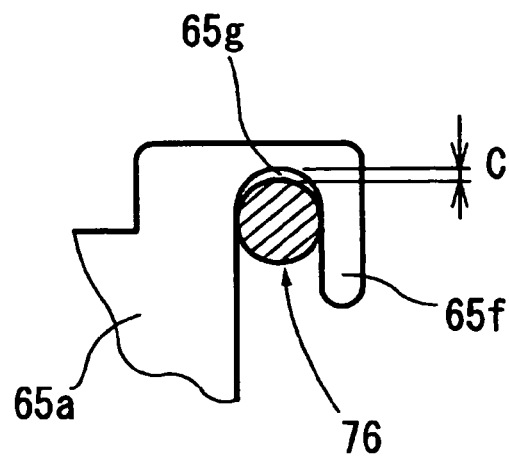
FIG. 11B is a vertical cross sectional view taken along line A2-A2 in FIG. 10.

The holding mechanism 3 assembled thus is mounted on the mounting table 64 placed in the apparatus main body 2 as shown in FIG. 8B. In this state, as shown in FIGS. 11A and 11B, gaps C are respectively formed, between an outer circumference upper surface of the locking rod 76 and a bottom surface (upper surface in FIG. 11) of the locking groove 65g, and between an outer circumference upper surface of the notch groove 76a and a bottom surface (upper surface in FIG. 11) of the locking groove 65h.

The cartridge holder 61 is thus stably held by the upper surface 64e of the mounting table 64, a vertical direction position of the cartridge holder 61 is determined. Accordingly, even though the pressuring nozzle 41 is moved downward and the tip thereof is brought into contact with the upper end opening 11e of the cartridge 11 set on the cartridge holder 61, the posture of the cartridge holder 61 is stable and does not tilt.

Moreover, at this time, the moving head 40 locates just above the waste liquid container 57 to open a space above the cartridge 11.

Further, when the movement operation member 31 is operated upward by the driving of the elevating/lowering motor 47 (see FIG. 4), a pair of positioning pins 31a is engaged with a pair of positioning holes 62d of the container holder 62 so that a relative position of the movement operation member 31 to the container holder 62 is determined.

Figure 13:
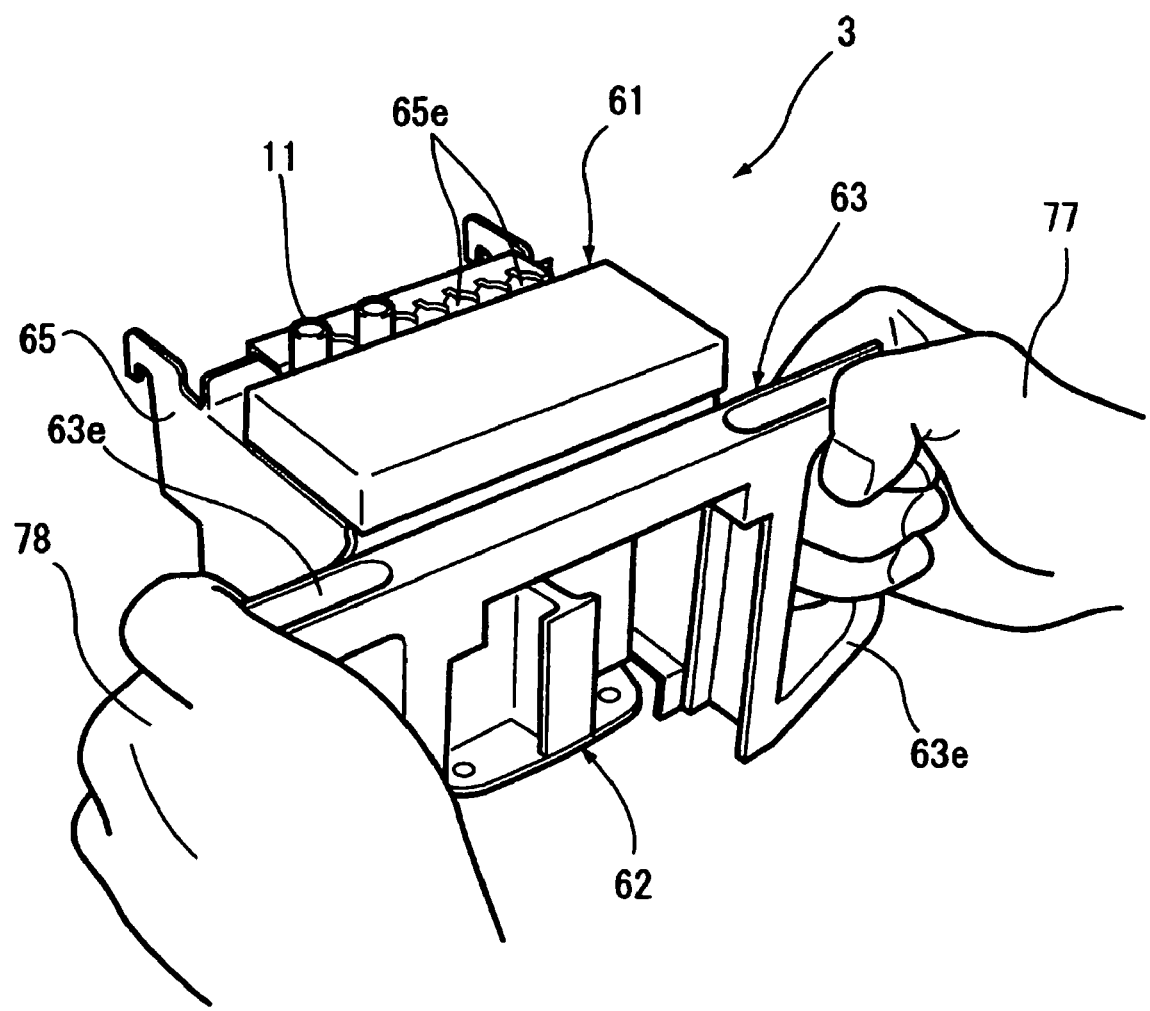
FIG. 13 is a perspective view showing a state that a gripping member of the holding mechanism is held with both hands and the holding mechanism is attached to the apparatus main body.
Figure 14:
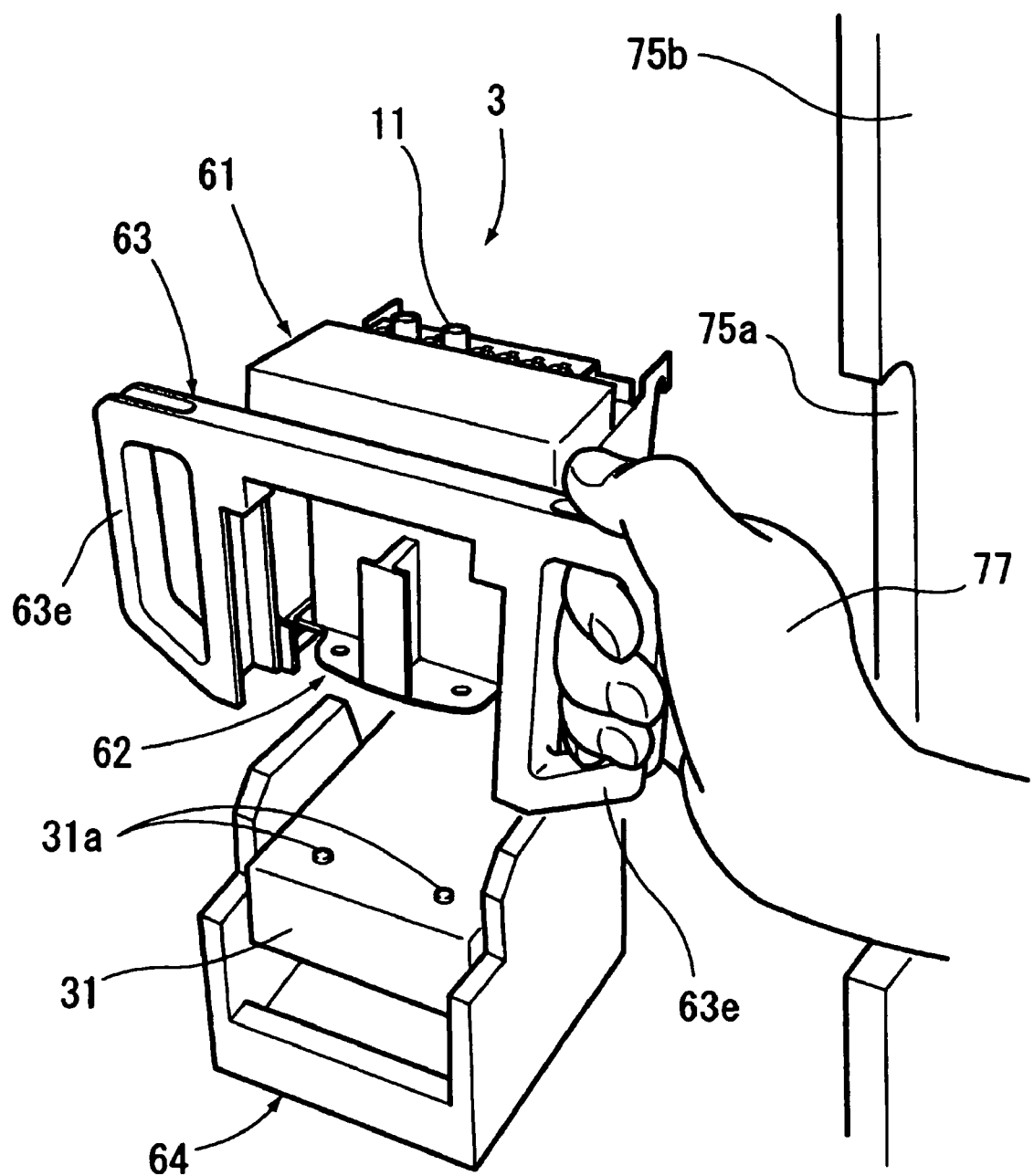
FIG. 14 is a perspective view showing a state that the gripping member of the holding mechanism is held with one hand and the holding mechanism is attached to the apparatus main body.

Mounting work of the holding mechanism on the mounting table 64 may be performed by gripping the pair of gripping members 63e with both hands 77 and 78 as shown in FIG. 13, or may be performed by gripping the holding member 63e with a right hand which is a dominant hand as shown in FIG. 14. The holding members 63e are provided at both sides of the container holding table 63 respectively, and therefore it is a matter of course that when a left hand is the dominant hand, the gripping member may be gripped with the left hand. In either mounting work, the concave portions 75a, which cave into a rear side of the main body portion 75 from a front side thereof, are provided at the side walls 75b of the front sides of the main body portion 75 respectively so that the work space is ensured, and therefore when the holding mechanism 3 is attached to or detached from the apparatus main body 2, the hands gripping the container holding table 63, etc., do not interfere with the main body portion 75, and the work can be made easy.

Moreover, in the above explanation, the sample solution S subjected to the dissolution treatment is injected into the cartridge 11 held by the mounting mechanism 3, and then the holding mechanism 3 is mounted on mounting table 64. However, the sample solution S may be injected into the cartridge 11 in the apparatus main body 2 after the holding mechanism 3 is mounted on mounting table 64.

Thereafter, when the apparatus is operated by the operation of the operation panel 71, the moving head 40 moves to the position just above the cartridge 11. The pressuring nozzle 41 is arranged just above a predetermined cartridge, and the pressuring nozzle 41 of the moving head 40 is moved downward by driving of a nozzle elevating/lowering motor 81 of the pressurized air feeding mechanism 4 so that the outer circumference surface of the tip of the pressuring nozzle 41 is brought into close contact with the tilted surface 11f of the cartridge 11 (see FIG. 21).

Figure 15A:
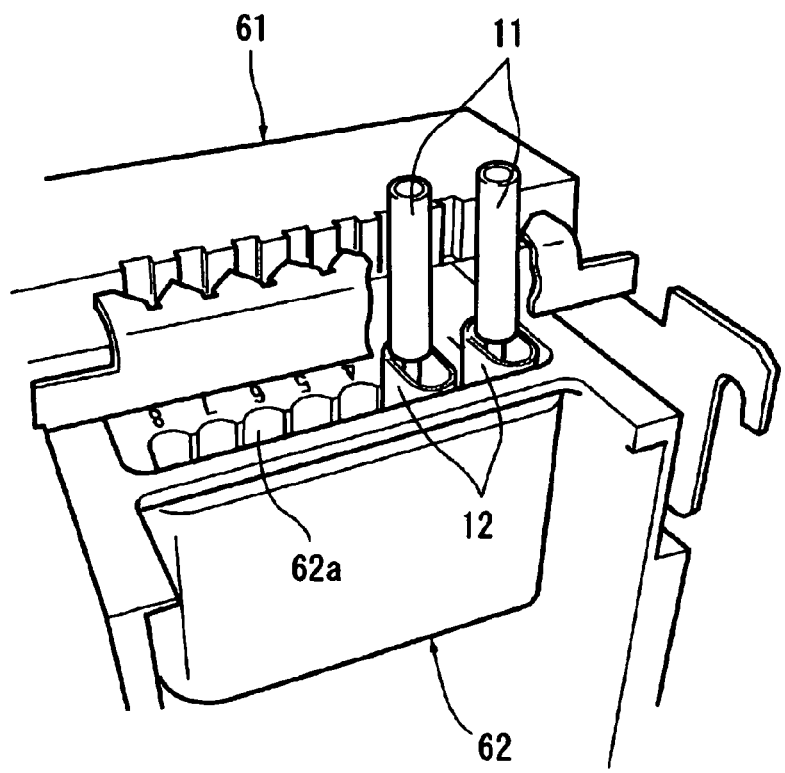
FIG. 15A is a main portion broken perspective view showing a state that a cartridge is positioned above a waste liquid container.

The container holder 62 is elevated by the driving of the movement operation member 31 and the lower end drain portion 11c of the cartridge 11 is inserted into the waste liquid container 12 at the predetermined amount (see FIG. 15A), so that the drain liquid is not leaked outside by splattering, etc., and no contamination occurs.

And then, the pressurized air is fed. The air pump 43 is driven by the instruction from the control portion 70 with the switching valve 45 in a closed state, and the switching valve 45 is operated to open. The predetermined amount of the pressurized air is fed into the first cartridge 11 from the air pump 43 via the pressuring nozzle 41.

Next, the switching valve 45 is operated to close, and the pressuring nozzle 41 is elevated by the nozzle elevating/lowering motor 81 so that the moving head 40 is moved at an arrangement pitch between the cartridges 11 by the driving of the head moving motor 26. Then, the predetermined amount of the pressurized air is similarly fed into the second cartridge 11.

The sample solution S, to which a pressure is applied, passes through the nucleic acid adsorptive porous membrane 11b, and the nucleic acid contained therein is adsorbed thereto and held, and the other liquid component is drained into the waste liquid container 12 through the drain portion 11c of the lower end of the cartridge 11. Once the entire sample solution S passes through the nucleic acid adsorptive porous membrane 11b, pressure lowers to a liquid drain completion pressure or less, the pressure sensor 46 detects finish of extraction of the cartridge 11. The process is repeated by only the number of cartridges.

Next, washing treatment is started. The moving head 40 is elevated to be returned above the first cartridge 11 after feeding of the pressurized air. The washing solution dispensing nozzle 51w of the moving head 40 is made to stop above the first cartridge 11 to dispense the predetermined amount of the washing solution W into the cartridge 11, and the moving head 40 is moved to the next cartridge 11 so that the washing solution W is dispensed into the cartridges 11 in order. When dispensing the washing solution W into all the cartridges 11 is finished, the moving head 40 is returned above the first cartridge 11.

Next, the pressuring nozzle 41 of the moving head 40 lowers, the lower end of the pressuring nozzle 41 is brought into pressure contact with the upper end opening 11e of the cartridge 11 to seal the opening 11e, and thereafter the switching valve 45 is opened similarly to the above-described so that the pressurized air is fed into the cartridge 11. The washing solution W, to which the pressure is applied, passes through the nucleic acid adsorptive porous membrane 11b to wash and remove an impurity other than the nucleic acid, the washing solution W is drained from the drain portion 11c of the lower end of the cartridge 11 into the waste liquid container 12. When the washing solution W in all the cartridges 11 passes through the nucleic acid adsorptive porous membrane 11b to be drained, the moving head 40 is returned to an initial position. Moreover, the operation described above is repeated when the washing treatment is performed several times.

Next, recovering treatment is started. First, the container holder 62 is operated downward by the elevating motor 47 synchronized with return operation of the moving head 40 after the washing treatment, the drain portion 11c of the lower end of the cartridge 11 is taken out from the waste liquid container 12, and thereafter the movement operation member 31 is moved by the driving of the container exchange motor 32 so that the container holder 62 is moved backward. Thus, an exchange of the container that the recovering container 13 is positioned under the cartridge 11 is performed.

Figure 15B:
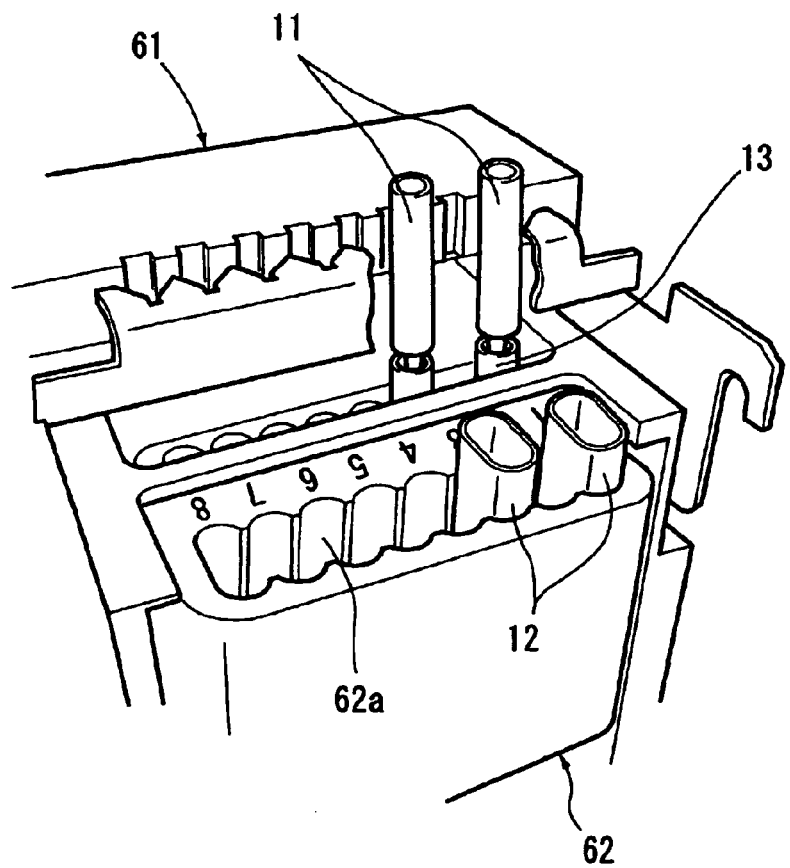
FIG. 15B is a main portion broken perspective view showing a state that a cartridge is positioned above a recovering container.

Subsequently, as shown in FIG. 15B, the container holder 62 is elevated by the elevating/lowering motor 47 and held in a state that the lower end of the cartridge 11 is inserted into the recovering container 13. The moving head 40 is moved so that the recovering solution dispensing nozzle 51r is stopped above the first cartridge 11 to dispense the predetermined amount of the recovering solution R into the cartridge 11, and the moving head 40 is moved to the next cartridge 11 so that dispensing the recovering solution R into the cartridge is performed in order. When dispensing the recovering solution R into all the cartridges 11 is finished, feeding the pressurized air to each cartridge is performed similarly to the above-described.

The pressurized air is fed into the cartridge similarly to the above-described, the recovering solution, to which the pressure is applied, passes through the nucleic acid adsorptive porous membrane 11b to detach the nucleic acid adsorbed thereto, and the nucleic acid is drained into the recovering container 13 from the drain portion 11c of the lower end of the cartridge 11 together with the recovering solution R. When the recovering solution R in all the cartridges 11 is entirely drained into the recovering containers 13, the moving head 40 is moved to a waiting position just above the first waste liquid container 57, and a series of operations finishes.

The container holder 62, that the extraction operation finishes, is lowered by the driving of the elevating/lowering motor 47, engagement of the positioning holes 62d of the container holder 62 with the positioning pins 31a of the movement operation member 31 is released, the holding mechanism 3 constituted by the cartridge holder 61, the container holder 62 and the container holding table 63 is collectively taken out from the apparatus main body 2.

Further, the cartridges 11 and the waste liquid containers 12 are respectively taken from the cartridge holder 61 and the container holder 62 to be discarded. On the other hand, the recovering containers 13 are taken out from the container holder 62 to be capped and subjected to the next nucleic analysis treatment, etc., if necessary.

Here, air fed from the air pump 43 into the cartridge 11 may be any gas as long as it does not have influence on the quality of the sample solution, the washing solution, the recovering solution and the like.

Further, when a plurality of holding mechanisms 3 (cartridge holders 61, container holders 62 and container holding tables 63) are prepared, preparation work of the next sample solution S can be performed during the above-described nucleic acid extraction operation, and more efficient continuous extraction work is realized.

<Modification>

Next, modification of the holding mechanism will be explained referring to FIG. 16 to FIG. 18.

Figure 16:
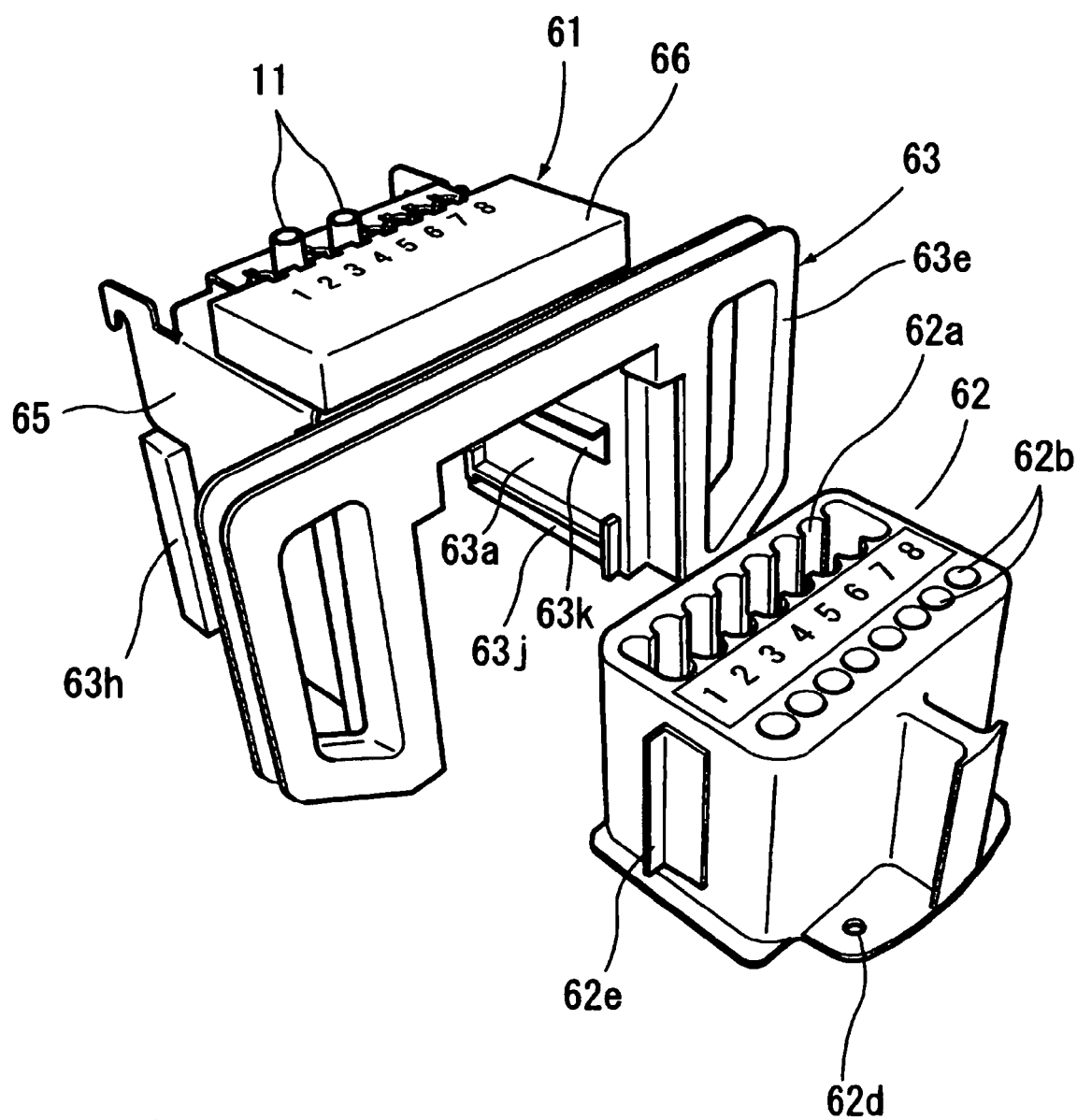
FIG. 16 is a perspective view of a modification of the holding mechanism.

FIG. 16 is a perspective view of the modification of the holding mechanism, FIG. 17 is plan view showing a state that the container holder is loaded from a correct direction and FIG. 18 is a plan view showing a state that the container holder is loaded from an incorrect direction.

As shown in FIG. 16, a vertical projection 62e extended in the vertical direction is projected on one of the outer side wall surfaces of the container holder 62 of the modification. When the container holder 62 is inserted into the container holding table 63 from the correct direction, a lateral projection 63k extended in the cross direction is projected and formed in an inward direction on the inside of the side wall 63a opposite the vertical projection 62e. Insertion direction regulating means for regulating the insertion direction of the container holder 62 to a specific direction is constituted by the vertical projection 62e of the container holder 62 and the lateral projection 63k of the container holding table 63.

Moreover, the other parts of the holding mechanism are similar to the holding mechanism 3 described above, and therefore the same symbols or corresponding symbols are attached to the same parts and overlapping explanations will be simplified or omitted.

Figure 17A:
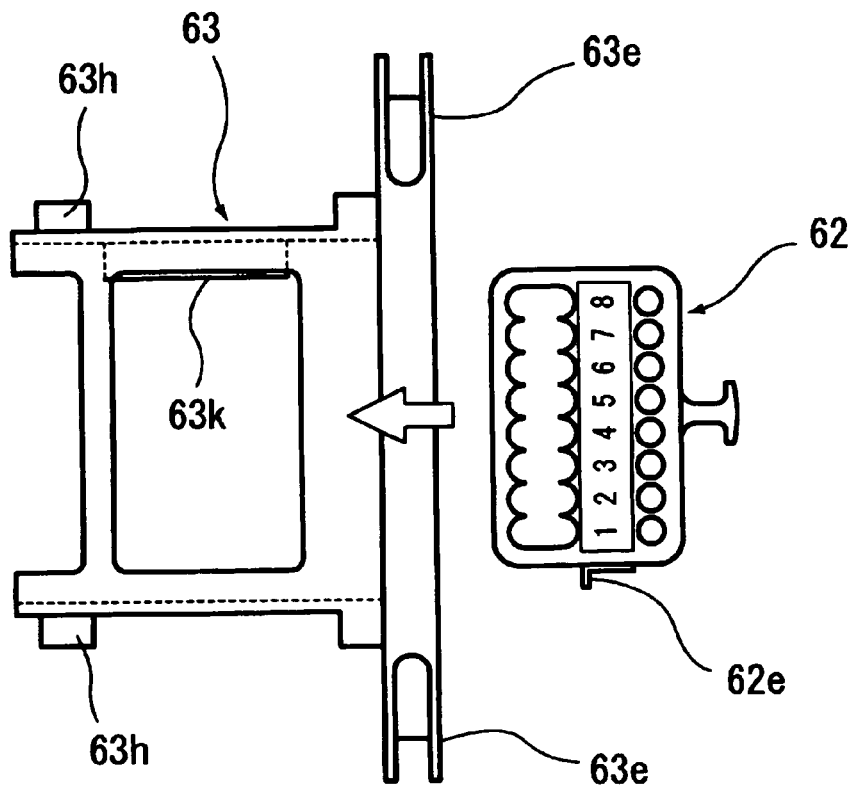
FIGS. 17A and 17B are plan views showing a state that the container holder shown in FIG. 16 is loaded onto the container holding table from a correct direction.
Figure 17B:
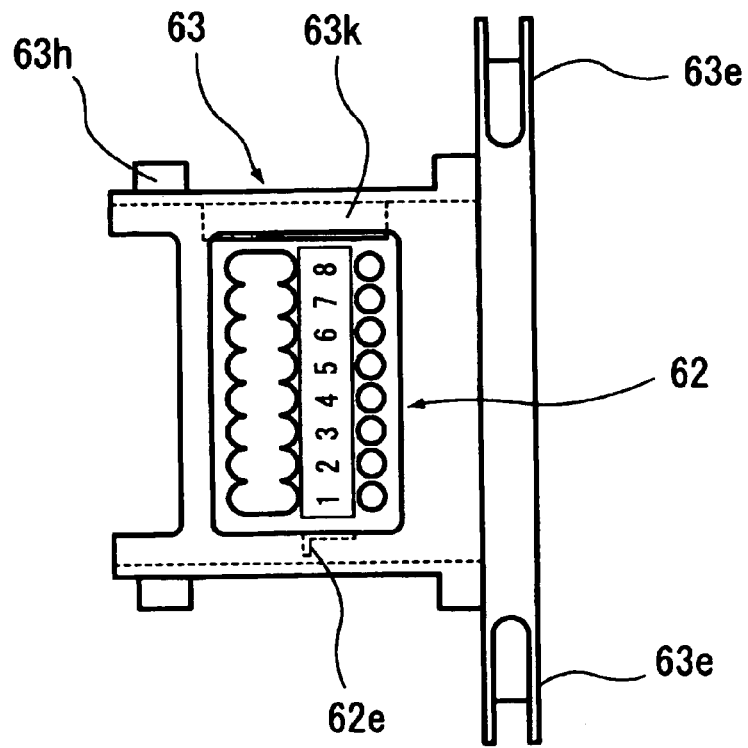
Figure 18A:
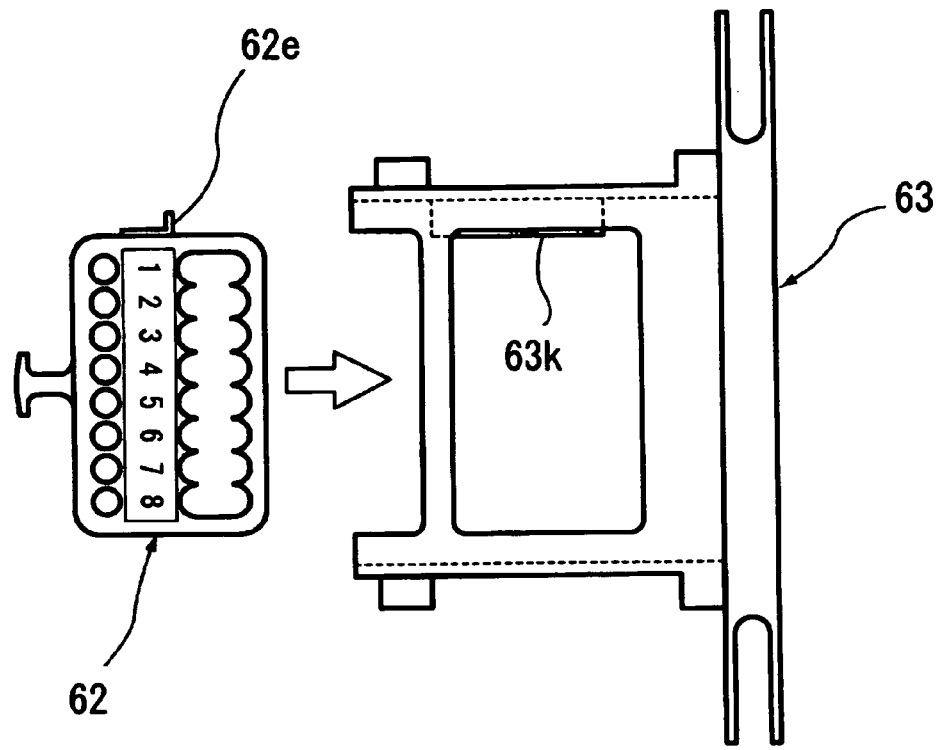
FIGS. 18A and 18B are plan views showing a state that the container holder shown in FIG. 16 is loaded onto the container holding table from an incorrect direction.
Figure 18B:
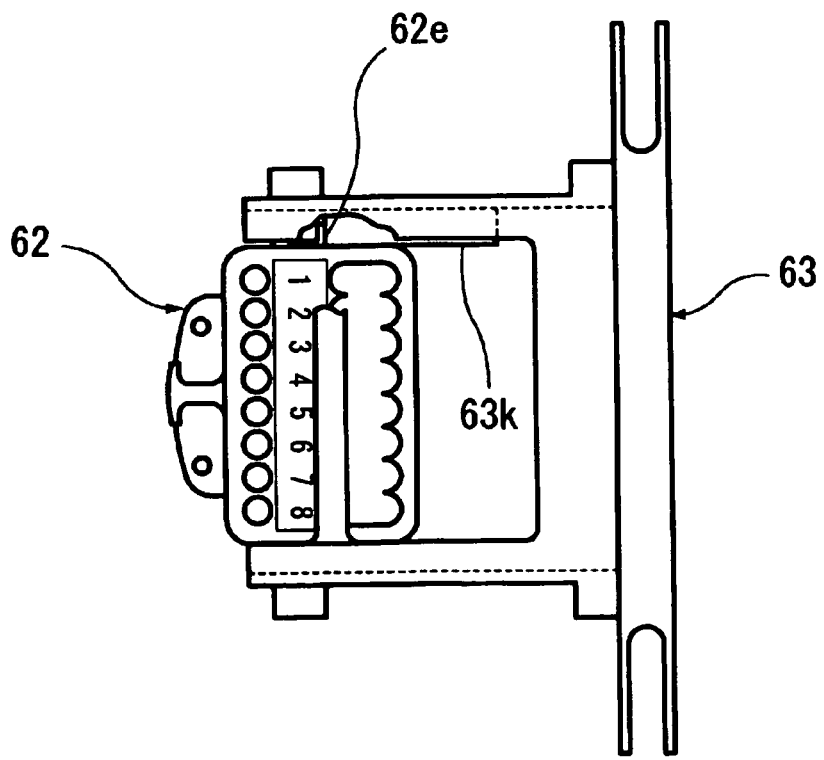
Figure 19:
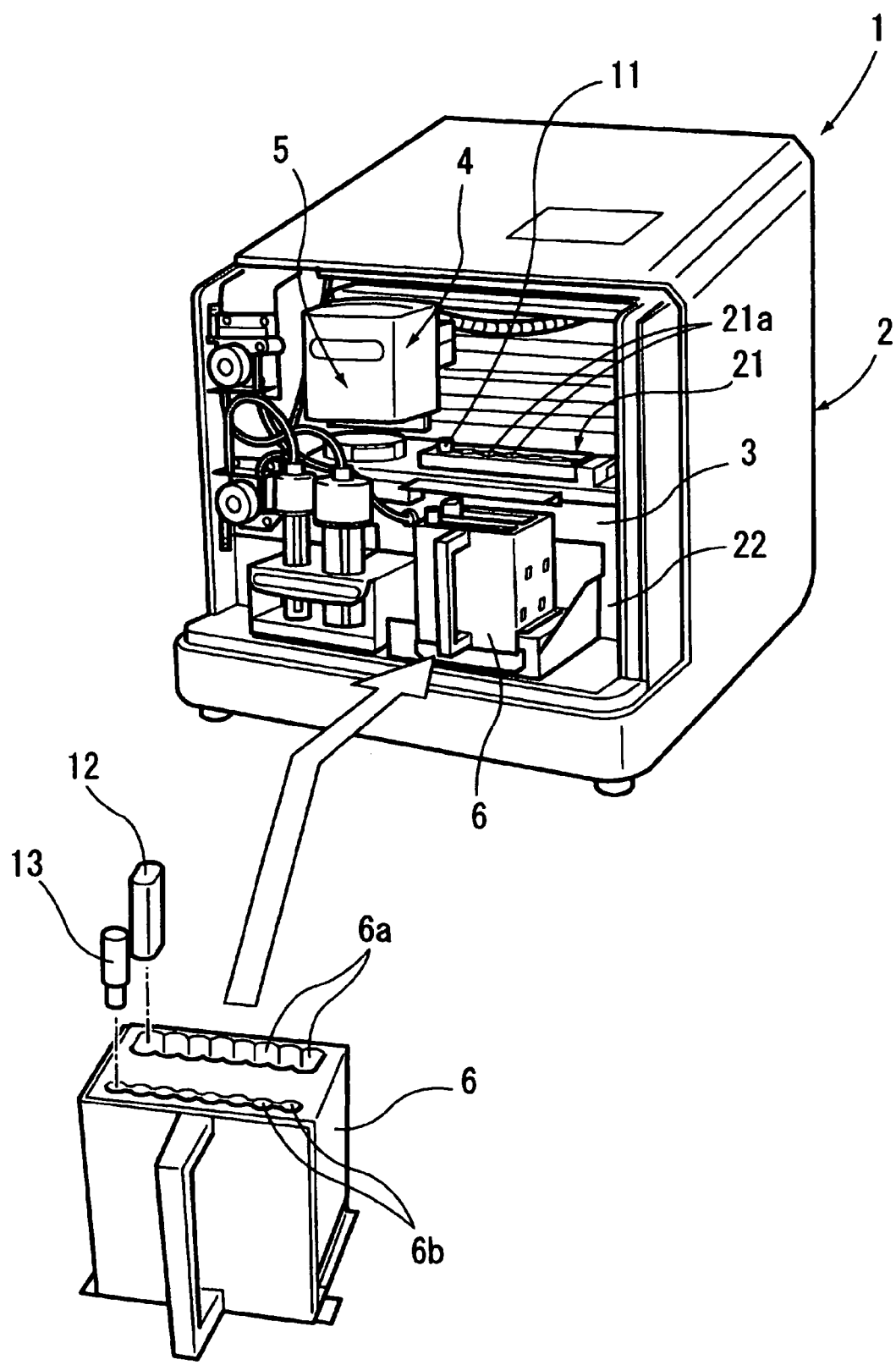
FIG. 19 is a perspective view showing a state that a rack is attached to a conventional apparatus for extracting nucleic acid.
Figure 20A:
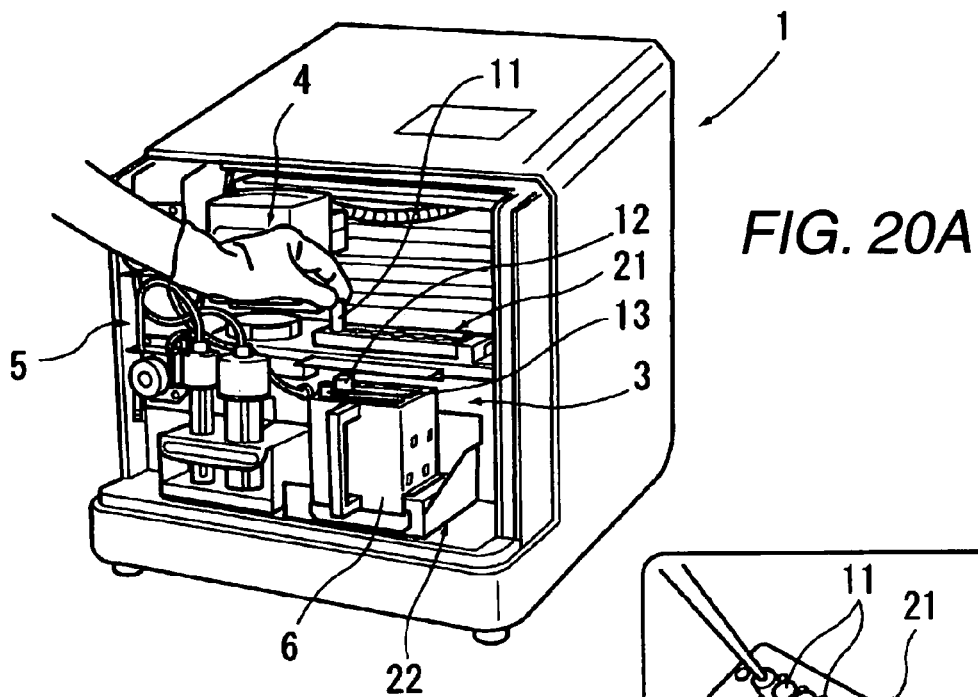
FIG. 20A to 20C are perspective views showing a process in which a cartridge is held by the conventional apparatus for extracting nucleic acid and then a sample solution is injected into the cartridge with a pipette.
Figure 20B:
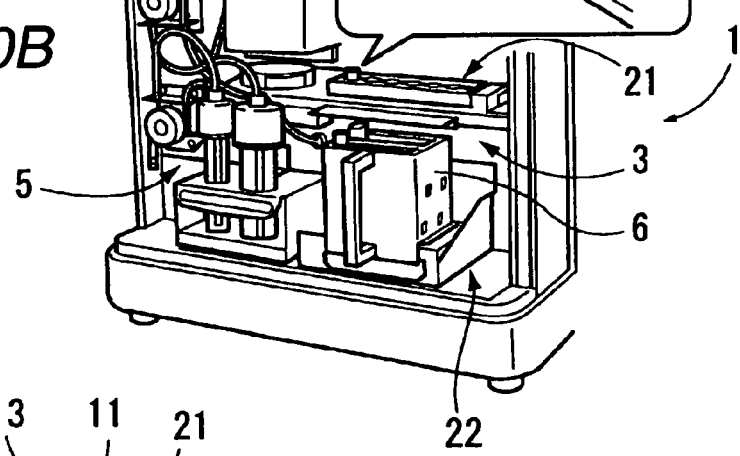
Figure 20C:
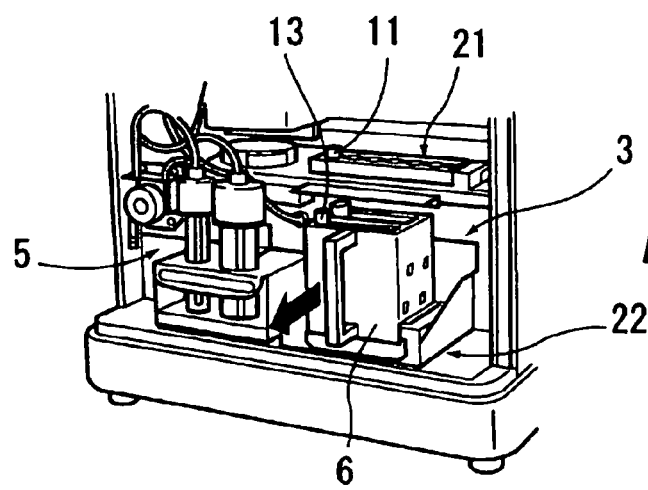

As shown in FIG. 17, when the container holder 62 is inserted into the container holding table 63 from the correct direction (see FIG. 17A), the vertical projection 62e of the container holder 62 and the lateral projection 63k of the container holding table 63 respectively locate at places opposite each other so as not to interfere with each other, the container holder 62 is mounted at a normal place of the container holding table 63 (see FIG. 17B). However, as shown in FIG. 18, when the container holder 62 is inserted into the container holding table 63 from the incorrect direction (see FIG. 18A), the vertical projection 62e of the container holder 62 and the lateral projection 63k of the container holding table 63 interfere with each other to prevent the insertion, and therefore a worker can easily recognize that the insertion direction is erroneous (see FIG. 18B). Thus, an erroneous insertion of the container holder 62 is prevented and nucleic acid extraction treatment can always be accurately and reliably performed.

Next, the nucleic acid adsorptive porous membrane (nucleic acid adsorptive porous body) 11b provided in the cartridge 11 will be explained in detail.

The nucleic acid adsorptive porous membrane 11b provided in the cartridge 11 is basically porous through which the nucleic acid is allowed to pass. A surface of the nucleic acid adsorptive porous membrane 11b is constituted so as to have a characteristic of adsorbing the nucleic acid contained in the sample solution by a chemical bonding force, to hold the adsorption during the washing by the washing solution and to weaken an adsorbing force of the nucleic acid during the recovery by the recovering solution and separate the nucleic acid.

The nucleic acid adsorptive porous membrane 11b provided in the nucleic acid extraction cartridge 11 is a porous membrane which adsorbs the nucleic acid by interaction in which an ionic bond is not substantially involved. Which means non-ionization as a usage condition of the porous membrane side, it is estimated that the nucleic acid and the porous membrane come to pull against each other by a change in polarity of surroundings. Thus, the nucleic acid adsorptive porous membrane 11b has excellent separation performance and improved washing efficiency and can isolate and purify the nucleic acid. It is preferable that the nucleic acid adsorptive porous membrane is a porous membrane having a hydrophilic group, and it is estimated that the nucleic acid and the hydrophilic group of the porous membrane come to pull against each other by the change in polarity of surroundings.

The hydrophilic group indicates a polar group (atomic group) capable of having interaction with water, and whole groups which involve the adsorption of the nucleic acid is applicable to the polar group. It is preferable that a group, of which strength of the interaction with the water is at an intermediate level, (see Item "Group of which hydrophilicity is not so strong" of Section "Hydrophilic group" of Chemical Encyclopedia published by Kyoritsu-Shuppan, Co., Ltd.) is employed as the hydrophilic group. For example, a hydroxyl group, carboxyl group, cyano group, oxyethylene group or the like is applicable, however, the hydroxyl group is more preferable.

Here, the porous membrane having the hydrophilic group means a porous membrane in which a material itself forming the porous membrane has the hydrophilic group or a porous membrane into which the hydrophilic group is introduced by a treatment or a coating of the material forming the porous membrane. The material forming the porous membrane may be either organic matter or inorganic matter. For example, a porous membrane in which the material itself forming the porous membrane is an organic material having the hydrophilic group, a porous membrane into which the hydrophilic group is introduced by treatment of a porous membrane of an organic material having no hydrophilic group, a porous membrane into which the hydrophilic group is introduced by coating the porous membrane of the organic material having no hydrophilic group with a material having the hydrophilic group, a porous membrane in which the material itself forming the porous membrane is an inorganic material having the hydrophilic group, a porous material into which the hydrophilic group is introduced by treatment of a porous membrane of an inorganic material having no hydrophilic group, a porous membrane into which the hydrophilic group is introduced by coating the porous membrane of the inorganic material having no hydrophilic group with the material having the hydrophilic group or the like can be employed. However, in view of facility of processing, it is preferable that an organic material such as an organic polymer is employed as the material forming the porous membrane.

As the porous membrane of the material having the hydrophilic group, a porous membrane of an organic material having the hydroxyl group can be cited. As the porous membrane of the organic material having the hydroxyl group, a porous membrane formed from polyhydroxyethylacrylic acid, polyhydroxyethylmethacrylic acid, polyvinyl alcohol, polyvinylpyrrolidone, polyacrylic acid, polymethacrylic acid, polyoxyethylene, acetylcellulose, a mixture of acetylcelluloses having different acetyl values or the like is applicable, however, especially, a porous membrane of an organic material having a polysaccharide structure is preferably employed.

A porous membrane of an organic polymer composed of the mixture of acetylcelluloses having different acetyl values is preferably employed as the porous membrane of the organic material having the hydroxyl group. As the mixture of acetylcelluloses having different acetyl values, a mixture of triacetylcellulose and diacetylcellulose, a mixture of triacetylcellulose and monoacetylcellulose, a mixture of triacetylcellulose, diacetylcellulose and monoacetylcellulose, or a mixture of diacetylcellulose and monoacetylcellulose is preferably employed.

Especially, the mixture of triacetylcellulose and diacetylcellulose is preferably employed. It is preferable that a mixing ratio (mass ratio) of the triacetylcellulose and diacetylcellulose is 99:1 to 1:99, and more preferable that the mixing ratio is 90:10 to 50:50.

As a more preferable organic material having the hydroxyl group, a surface-saponified matter of the acetylcellulose disclosed in Japanese Published Patent Application No. 2003-128691 is applicable. The surface-saponified matter of the acetylcellulose is a matter that the mixture of acetylcelluloses having different acetyl values is subjected to saponification treatment. As the surface-saponified matter of the acetylcellulose, a saponified matter of the mixture of triacetylcellulose and diacetylcellulose, a saponified matter of the mixture of triacetylcellulose and monoacetylcellulose, a saponified matter of the mixture of triacetylcellulose, diacetylcellulose and monoacetylcellulose, or a saponified matter of the mixture of diacetylcellulose and monoacetylcellulose is preferably employed. It is more preferable that the saponified matter of the mixture of triacetylcellulose and diacetylcellulose is employed. It is preferable that the mixing ratio (mass ratio) of the triacetylcellulose and diacetylcellulose is 99:1 to 1:99, and more preferable that the mixing ratio of the triacetylcellulose and diacetylcellulose is 90:10 to 50:50. In this case, an amount (density) of the hydroxyl group of a solid surface can be controlled based on the degree of saponification treatment (saponification rate). In order to raise separation efficiency of the nucleic acid, it is preferable that the amount (density) of the hydroxyl group increases. For example, in acetylcellulose such as triacetylcellulose, it is preferable that the saponification rate (surface-saponification rate) is about 5% or more, more preferable that it is 10% or more. Further, in order that a surface area of the organic polymer having the hydroxyl group is enlarged, it is preferable that the porous membrane of acetylcellulose is subjected to the saponification treatment. In this case, the porous membrane may be a two sided-symmetrical porous membrane, however, a two sided-non-symmetrical porous membrane is preferably employed.

The saponification treatment means that the acetylcellulose is brought into contact with a saponification treatment liquid (for example, sodium hydroxide aqueous solution). Thus, a part of the acetylcellulose brought into contact with the saponification treatment liquid becomes a regenerated cellulose and the hydroxyl group is introduced thereinto. The regenerated cellulose thus produced is different from an original cellulose in terms of a crystal state, etc.

Further, the saponification treatment may be performed by a change of concentration of the sodium hydroxide aqueous solution in order to change the saponification rate. The saponification rate can be easily measured by NMR, IR or XPS. (for example, the rate can be measured with the degree of peak reduction of carbonyl group.)

As a method for introducing the hydrophilic group into the porous membrane of the organic material having no hydrophilic group, there is a method for bonding a graft polymer chain having the hydrophilic group in a chain or side chain of the polymer with the porous membrane.

As a method for bonding the graft polymer chain with the porous membrane of the organic material, there are two methods: that the porous membrane is chemically bonded with the graft polymer chain; and that the compound having a polymerizable double bond are polymerized with the porous membrane as a starting point so as to form the graft polymer.

In the method for adhering the graft polymer chain to the porous membrane by chemical bond, a polymer having a functional group reacting with the porous membrane in an end or side chain thereof is used, the polymers can be made to graft by chemical reaction between the functional group and a functional group of the porous membrane. The functional group reacting with the porous membrane is not particularly limited, as long as a functional group can react with the functional group of the porous membrane. However, for example, a silane coupling group such as alkoxysilane, isocyanate group, amino group, hydroxyl group, carboxyl group, sulfonic acid group, phosphate group, epoxy group, allyl group, methacryloyl group, acryloyl group or the like is applicable.

As an especially useful compound as a polymer having a reactive functional group in the end or side chain thereof, a polymer having trialkoxysilyl group in the polymer end, a polymer having an amino group in the polymer end, a polymer having a carboxyl group in the polymer end, a polymer having an epoxy group in the polymer end, a polymer having an isocyanate group in the polymer end can be cited. The polymer used at this time is not particularly limited, as long as a polymer has a hydrophilic group involving the absorption of the nucleic acid. However, for example, polyhydroxyethylacryl acid, polyhydroxyethylmethacryl aid and salt thereof, polyvinyl alcohol, polyvinylpyrrolidone, polyacryl acid, polymethacryl acid and salt thereof, polyoxyethylene or the like is applicable.

The method for forming the graft polymer chain by polymerization of the compound having the polymerizable double bond with the porous membrane as a starting point is generally called surface graft polymerization. The surface graft polymerization method indicates a method that an active species is provided on a surface of a base material by a method such as plasma irradiation, optical irradiation and heating so that the compound, which is arranged so as to come into contact with the porous membrane and have the polymerizable double bond, is bonded with the porous membrane by the polymerization.

A compound which is useful for farming the graft polymer chain bonding with the base material is required to have two characteristics, having the polymerizable double bond and having the hydrophilic group involving the adsorption of the nucleic acid. As such a compound, any of the compounds, polymer, oligomer, and monomer respectively having the hydrophilic group, may be employed as long as it has the double bond in a molecule. An especially useful compound is the monomer having a hydrophilic group.

As an especially useful monomer having a hydrophilic group, for example, a monomer containing a hydroxyl group of 2-hydroxyethylacrylate, 2-hydroxyethylmethacrylate, glycerolmonomethacrylate or the like is preferably employed. Further, a monomer containing a carboxyl group of acryl acid, methacryl acid or the like, alkali metal salt thereof or amine salt thereof is also preferably employed.

As another method for introducing the hydrophilic group into the porous membrane of the organic material having no hydrophilic group, a method for coating a material having the hydrophilic group is cited. The material used for the coating is not particularly limited, as long as the material has the hydrophilic group involving the adsorption of the nucleic acid. It is however preferable that polymer of the organic material is employed in terms of facility of work. As the polymer, polyhydroxyethylacryl acid, polyhydroxyethylmethacryl acid and salt thereof, polyvinyl alcohol, polyvinylpyrrolidone, polyacryl acid, polymethacryl acid and salt thereof, polyoxyethylene, acetylcelluloses, the mixture of acetylcelluloses having different acetyl values or the like is applicable, however, it is preferable that a polymer having the polysaccharide structure is employed.

Further, the porous membrane of the organic material having no hydrophilic group of the acetylcelluloses or the mixture of acetylcelluloses having different acetyl values may be coated with the acetylcelluloses or the mixture of acetylcelluloses having different acetyl values to be subjected to the saponification treatment. In this case, it is preferable that the saponification rate is about 5% or more, and more preferable is 10% or more.

As the porous membrane of the inorganic material having the hydrophilic group, a porous membrane containing a silica compound can be cited. As the porous membrane containing the silica compound, a glass filter can be cited. Further, a porous silica thin film disclosed in Patent Publication No. 3058342 can be cited. The porous silica thin film can be produced in such a way that after a developing liquid of a cation type amphiphilic material having a bimolecular membrane formability is developed on a base, a thin film of a multi-layer bimolecular membrane of the amphiphilic material is prepared by removal of a solvent from a liquid film on the base, the thin film of the multi-layer bimolecular membrane is brought into contact with a solution containing the silica compound to be extracted and removed.

As a method for introducing the hydrophilic group into the porous membrane of the inorganic material having no hydrophilic group, there are two methods: that the porous membrane is chemically bonded with the graft polymer chain; and that the graft polymer is polymerized with the porous membrane as a starting point by use of the monomer having the hydrophilic group with the double bond in the molecule.

When the porous membrane is adhered to the graft polymer chain by the chemical bond, a functional group which reacts with the functional group of the end of the graft polymer is introduced into the inorganic material and the graft polymer is chemically bonded with the introduced inorganic material. Further, when that the graft polymer is polymerized with the porous membrane as a starting point by use of the monomer having the hydrophilic group with the double bond in the molecule, a functional group which becomes a starting point during the polymerization of the compound having the double bond is introduced into the inorganic material.

As a graft polymer having the hydrophilic group and the monomer having the hydrophilic group having the double bond in the molecule, the graft polymer having the hydrophilic group and the monomer having the hydrophilic group with the double bond in the molecule, which are described in the method that the porous membrane of the organic material having no hydrophilic group is chemically bonded with the graft polymer chain, are preferably employed.

As another method for introducing the hydrophilic group into the porous membrane of the inorganic material having no hydrophilic group, a method that a material having the hydrophilic group is subjected to the coating can be cited. The material used for the coating is not particularly limited, as long as the material has the hydrophilic group involving the adsorption of the nucleic acid, however, it is preferable that the polymer of the organic material is employed in terms of the facility of work. As the polymer, polyhydroxyethylacryl acid, polyhydroxyethylmethacryl acid and salt thereof, polyvinyl alcohol, polyvinylpyrrolidone, polyacryl acid, polymethacryl acid and salt thereof, polyoxyethylene, acetylcelluloses, the mixture of acetylcelluloses having different acetyl values or the like is applicable.

Further, after the porous membrane of the inorganic material having no hydrophilic group is coated with the acetylcelluloses or the mixture of acetylcelluloses having different acetyl values, the coated acetylcelluloses or the mixture of acetylcelluloses having different acetyl values may be subjected to the saponification treatment. In this case, it is preferable that the saponification rate is about 5% or more, more preferable is 10% or more.

As the porous membrane of the inorganic material having no hydrophilic group, a porous membrane produced by processing of metal such as aluminum, glass, cement, ceramics or new ceramics, silicone, activated carbon or the like is applicable.

The solution can pass through the above-described nucleic acid adsorptive porous membrane, the thickness of the porous membrane is 10 µm to 500 µm, more preferable is 50 µm to 250 µm. It is preferable that the thickness is made as thin as possible in terms of facility of washing.

A minimum hole diameter of the above-described nucleic acid adsorptive porous membrane, through which the solution is allowed to pass, is 0.22 µm or more, more preferable is 0.5 µm or more. It is preferable that the porous membrane, in which a maximum diameter-minimum diameter ratio is 2 or more, is employed. Thus, a surface area sufficient for the adsorption of the nucleic acid can be obtained, and clogging hardly occurs. It is more preferable that maximum diameter-minimum diameter ratio is 5 or more.

A porosity of the above-described nucleic acid adsorptive porous membrane, through which the solution is allowed to pass, is 50 to 95%, more preferable is 65 to 80%. Further, a bubble point is 0.1 to 10 kgf/cm$^2$, more preferable is 0.2 to 4 kgf/cm$^2$.

It is preferable that a pressure loss of the above-described nucleic acid adsorptive porous membrane, through which the solution is allowed to pass, is 0.1 to 100 kPa. Thus, a uniform pressure can be obtained during overpressure. It is more preferable that the pressure loss is 0.5 to 60 pKa. Here, the pressure loss means a lowest pressure necessary for making water pass a membrane thickness of 100 µm.

It is preferable that a water permeability of the above-described nucleic acid adsorptive porous membrane, through which the solution is allowed to pass, is 1 to 5000 mL in 1 minute per 1 cm$^2$ of the membrane when the water is made to pass through under a pressure of 1 kg/cm$^2$ at 25° C. It is more preferable that the water permeability is 5 to 100 mL in 1 minute per 1 cm$^2$ of the membrane when the water is made to pass through under a pressure of 1 kg/cm$^2$ at 25° C.

It is preferable that an adsorption amount of the nucleic acid per 1 mg of the above-described nucleic acid adsorptive porous membrane, through which the solution is allowed to pass, is 0.1 µg or more, and more preferable is 0.9 µg or more.

It is preferable that the above-described nucleic acid adsorptive porous membrane, through which the solution is allowed to pass, is a cellulose derivative which is not dissolved within 1 hour but dissolved within 48 hours when the porous membrane of a square of 5×5 mm is immersed in 5 mL trifluoroacetic acid. Further, it is more preferable that the nucleic acid adsorptive porous membrane is a cellulose derivative which is dissolved within 1 hour when the porous membrane of a square of 5×5 mm is immersed in the 5 mL trifluoroacetic acid, and which is not dissolved within 24 hours when the porous membrane of a square of 5×5 mm is immersed in 5 mL dichloromethane acid.

When the sample solution containing the nucleic acid is made to pass through the nucleic acid adsorptive porous membrane, it is preferable that the sample solution is made to pass from one surface to the other surface in a point that the liquid can be uniformly brought into contact with the porous membrane. When the sample solution containing the nucleic acid is made to pass through the nucleic acid adsorptive porous membrane, it is preferable that the sample solution is made to pass from large hole diameter side to small hole diameter side of nucleic acid adsorptive porous membrane in a point that clogging hardly occurs.

It is preferable that a flow velocity when the sample solution containing the nucleic acid is made to pass through the nucleic acid adsorptive porous membrane is 2 to 1500 $\mu$L/sec per 1 $cm^2$ of the membrane so that a proper contact time of the liquid with the porous membrane can be obtained. When the contact time of the liquid with the porous membrane is too short, a sufficient nucleic acid extraction effect cannot be obtained, to the contrary when being too long, operability lowers. Further, it is preferable that the flow velocity is 5 to 700 $\mu$L/sec per 1 $cm^2$ of the membrane.

The nucleic acid adsorptive porous membrane, through which the solution is allowed to pass, may be used not only with one sheet but a plurality of sheets. The plurality of sheets of the nucleic acid adsorptive porous membranes may be all the same or different from each other.

The plurality of sheets of the nucleic acid adsorptive porous membranes also may be a combination of the nucleic acid adsorptive porous membrane(s) of the inorganic material and the nucleic acid adsorptive porous membrane(s) of the organic material. For example, a combination of the glass filter(s) and the porous membrane(s) of the regenerated celluloses can be cited. The plurality of sheets of the nucleic acid adsorptive porous membranes also may be a combination of the nucleic acid adsorptive porous membrane(s) of the inorganic material and the nucleic acid non-adsorptive porous membrane (s) of the organic material. For example, a combination of the glass filter(s) and the porous membrane(s) of nylon or polysulfone can be cited.

Further, the nucleic acid adsorptive porous membranes explained above are made of a shape other than the membrane in accordance with the shape of the cartridge. For example, a tip-shape, a block-shape or the like is applicable.

Figure 23:
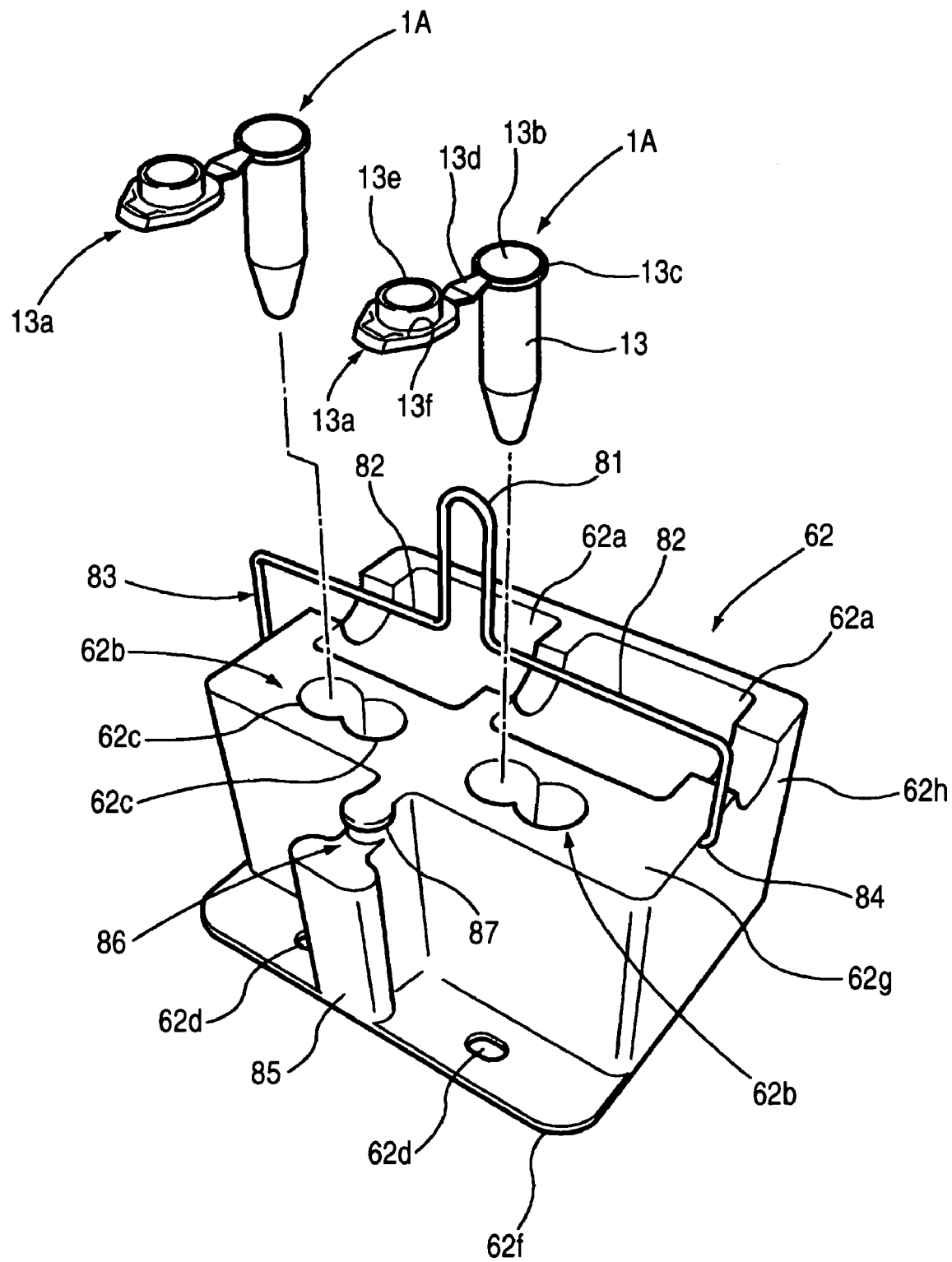
FIG. 23 is a perspective view of an apparatus for inserting and erecting a microtube according to the present invention.
Figure 24:
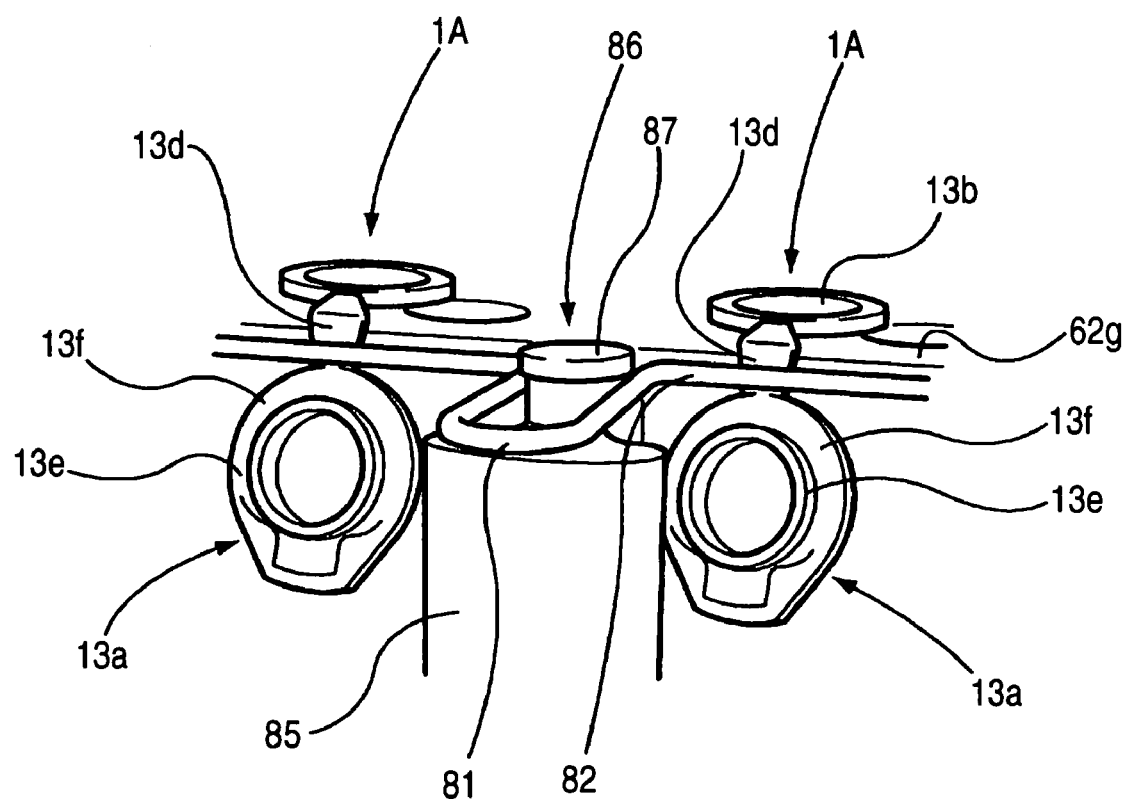
FIG. 24 is a main portion perspective view of the locking mechanism.

FIG. 23 is a perspective view of an apparatus for inserting and erecting a microtube according to the present invention, FIG. 24 is a perspective view of a main portion of the locking mechanism.

The apparatus for inserting and erecting a microtube 90 includes a press-bending member 83 provided on the casing 62. The casing 62 is integrally formed of a synthetic resin material, etc., in the block-shape. A brim portion 62f is extended from a front lower one side portion of the casing 62, the positioning holes 62d are bored in the brim portion 62f. The apparatus for inserting and erecting a microtube 90 is set at the predetermined position of the apparatus for automatically extracting nucleic acid (not shown) via the positioning holes 62d.

A plurality of insertion ports 62b, into which the microtubes with the cap 1a are inserted and erected, are juxtaposed in a line-shape on the upper surface 62g of the casing 62. Further, in the embodiment, two insertion ports 62b are respectively formed in a shape that the two circle-shaped holes connect.

The microtubes with the cap 1A can be inserted into any of the insertion ports.

The microtubes with the cap 1a inserted and erected into the insertion port 62b have the tube main body 13, the flange portion 13c provided on the circumferential edge of the tube opening portion 13b, the hinge portion 13d which connects the cap portion 13a with flange portion 13c and a cylinder portion 13e projected on a flange portion close contact surface 13f of the cap portion 13a and inserted into the tube opening portion 13b.

Liquid drain portions 62a are opened behind the insertion ports 62b of the upper surface 62g of the casing 62. The waste liquid container, which houses a waste liquid drained from the cartridge before dispensing of the nucleic acid in the apparatus for automatically extracting nucleic acid, is inserted into the liquid drain portion 62a. Alternatively, the waste liquid may be directly housed in the liquid drain portion 62a with no insertion of the waste liquid container. A shaft 84 of the press-bending member 83 is rotatably inserted into and supported by right and left side surfaces of the integrated liquid drain portions 62a of the casing 62. The press-bending member 83 becomes rotatable around the shaft 84 of a juxtaposition direction of the insertion ports 62b. The press-bending member 83 can be formed of a cross section circle-shaped wire rod made of stainless steel, etc. That is, the wire rod is bent in the substantial C-shape, both ends thereof as the shaft 84 are inserted into and supported by the casing 62. A U-shaped tab portion 81, which is also used as a component of the locking mechanism described later, is formed at the center portion of the wire rod.

A cross section ellipse-shaped column portion 85 is integrally erected with the casing 62 on the front side of the casing 62, an engaging projection portion 87, which is fitted to the inside of the tab portion 81, is formed on an upper portion of the column portion 85. The tab portion 81 and the engaging projection portion 87 constitute locking mechanism 86. A width of the engaging projection portion 87 is formed so as to be slightly larger than an inner width of the tab portion 81. The tab portion 81 is rotated to the front side of the casing 62 to come into contact with the engaging projection portion 87, and the tab portion 81 is further pressed down to be elastically deformed in a enlarged direction, and therefore the press-bending member 83 is engaged (locked) with the engaging projection portion 87. The tab portion 81 is lifted with a predetermined force to be elastically deformed again in the enlarged direction, and thus engagement release (lock release) can be performed.

As shown in FIG. 24, right and left horizontal wire rod portions 82 sandwiching the tab portion 81, are arranged so as to be slightly lower than an upper surface 62g of the casing 62 with the press-bending member 83 locked by the locking mechanism 86. Accordingly, in the microtube with the cap 1A of which the tube main body 13 is inserted into the insertion port 62b, when the press-bending member 83 is rotated until a position of being locked by the locking mechanism 86, the horizontal wire rod portion 82 press-bends the hinge portion 13d downward, and consequently the cap portion 13a positioned by the tip of the hinge portion 13*d* is press-bent and held at a perpendicular angle so as to be substantially parallel with the front surface of the casing 62.

Next, operation of the apparatus for inserting and erecting a microtube as thus constituted will be explained.

FIG. 25 are operation explanation views showing a press-bending holding operation of the cap portions of the apparatus for inserting and erecting a microtube as shown in FIG. 23.

Figure 25A:
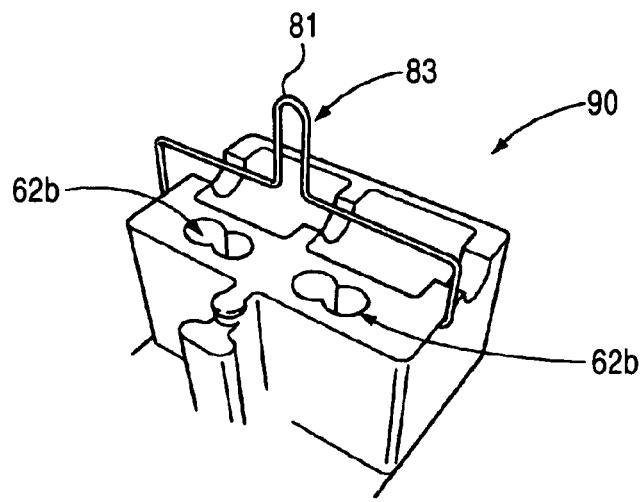
FIG. 25A to 25D are operation explanation views showing a press-bend hold operation of a cap portion of the apparatus for inserting and erecting a microtube shown in FIG. 23.
Figure 25B:
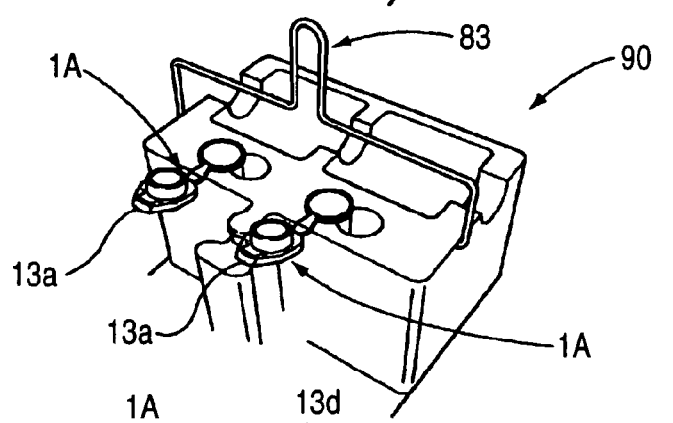

In the apparatus for inserting and erecting a microtube 90, first, in advance of insertion of the mictotube with the cap 1A, as shown in FIG. 25A, the tab portion 81 of the press-bending member 83 is gripped with fingers to be rotated and arranged upward. In this state, as shown in FIG. 25B, the mictotube with the cap 1A is inserted into the insertion port 62*b*. At this time, the mictotube with the cap 1A is arranged in a rotating direction such that the cap portion 13*a* projects from the front surface of the casing 62.

Figure 25C:
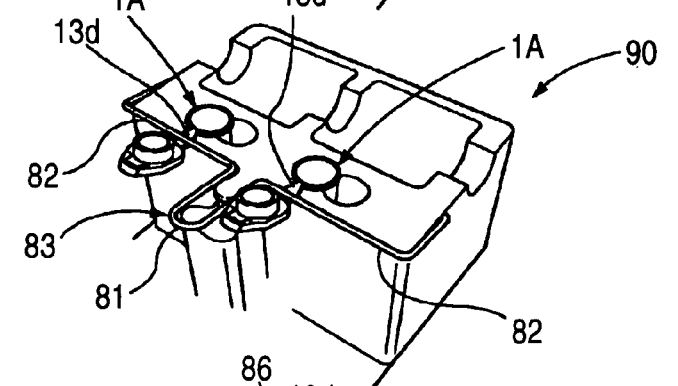
Figure 25D:
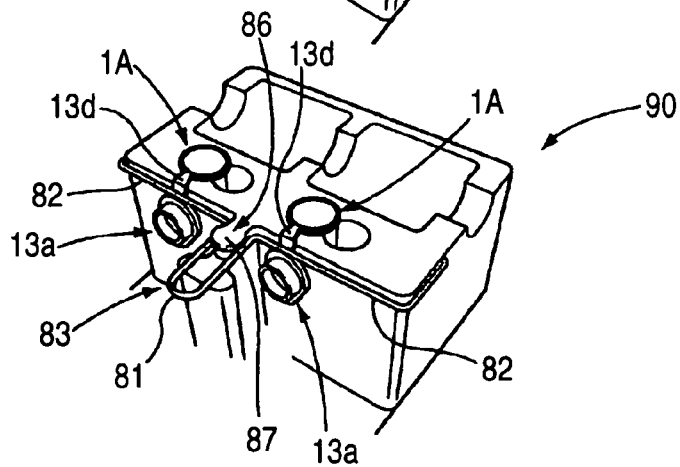

Next, as shown in FIG. 25C, the press-bending member 83 is made to rotate to the front side with the tab portion 81 of the press-bending member 83 gripped so that the horizontal wire rod portion 82 of the press-bending member 83 is brought into contact with the hinge portion 13*d*. When the press-bending member 83 is further press-bent downward in this state, in the microtube with the cap 1A, the hinge portion 13*d* is press-bent downward by the horizontal wire rod portion 82, the cap portion 13*a* positioned by the tip of the hinge portion 13*d* becomes substantially parallel with the front surface of the casing 62 to be pressed and bent. Further, in this state, as shown in FIG. 25D, the engaging projection portion 87 is engaged with the inside of tab portion 81. Thus, the press-bending member 83 is locked and held on the casing 62 by the locking mechanism 86 in a state of press-bending the cap portions 13*a*. In this state, the apparatus for inserting and erecting a microtube 90 is set in the apparatus for automatically extracting nucleic acid.

Moreover, even though the cap portion 13*a* of the microtube with the cap 1A is slightly tilted from an orthogonal direction to an arranging direction of the insertion ports 62*b* when the press-bending member 83 is pressed-down, a direction of the cap portion 13*a* is regulated by the press-bending member 83 so that the cap portion 13*a* is arranged in the orthogonal direction as shown in figure.

Accordingly, the cap portions 13*a* of the microtubes with the cap 1A inserted into the insertion portions 62*b* of the casing 62 are held by the press-bending member 83, the apparatus for inserting and erecting a microtube 90 is set in the apparatus for automatically extracting nucleic acid in this state, and thereafter even though vibration, etc., is applied to the casing 62, the cap portion 13*a* neither closes the opening portion 13*b* of the adjacent tube main body 13 nor comes into contact with a peripheral member. Thus, there is no possibility of causing obstruction of the apparatus performance.

The press-bending member 83 comes into contact with the hinge portion 13*d* to press-bend and hold the cap portion 13*a* not to be brought into contact with the cylinder portion 13*e* coming into contact with the inside of the tube main body 13 to which filth must not adhere, etc. Therefore, trouble such as occurrence of contamination is avoidable.

Further, the press-bending member 83 after press-bending of the cap portion 13*a* is held on the casing 62 via the locking mechanism 86, the cap portion 13*a* and the tube main body 13 is held immovably on the casing 62.

In the apparatus for inserting and erecting a microtube 90, the press-bending member 83, which press-bends and holds the cap portions 13*a* projected from the casing 62 downward, is rotatably provided. Accordingly, when the apparatus for inserting and erecting a microtube 90, which holds the microtubes with the cap 1A with the press-bending member 83, is set in the apparatus for automatically extracting nucleic acid in this state, even though vibration, etc., is applied thereto, the cap portion 13*a* neither closes the opening portion 13*b* of the adjacent tube main body 13 nor comes into contact with a peripheral member, so that there is no possibility of causing obstruction of the apparatus performance. Consequently, the apparatus for inserting and erecting a microtube 90 that injection trouble hardly occurs can be obtained.

Further, it becomes possible to fix the whole of microtube with the cap 1A via the cap portions 13*a* by the press-bending member 83, to prevent floating and tilting of the tube main body 13 due to an insertion error of the tube main body, and especially to improve an injection precision in automation. Furthermore, the tube main body 13 can be held on the casing 62 via the cap portion 13*a* by the press-bending member 83, therefore it is possible to move the casing itself at an optional angle in such a way that the casing 62 is tilted before injection of liquid.

Next, another embodiment of the apparatus for inserting and erecting a microtube according to the present invention will be explained.

Figure 26:
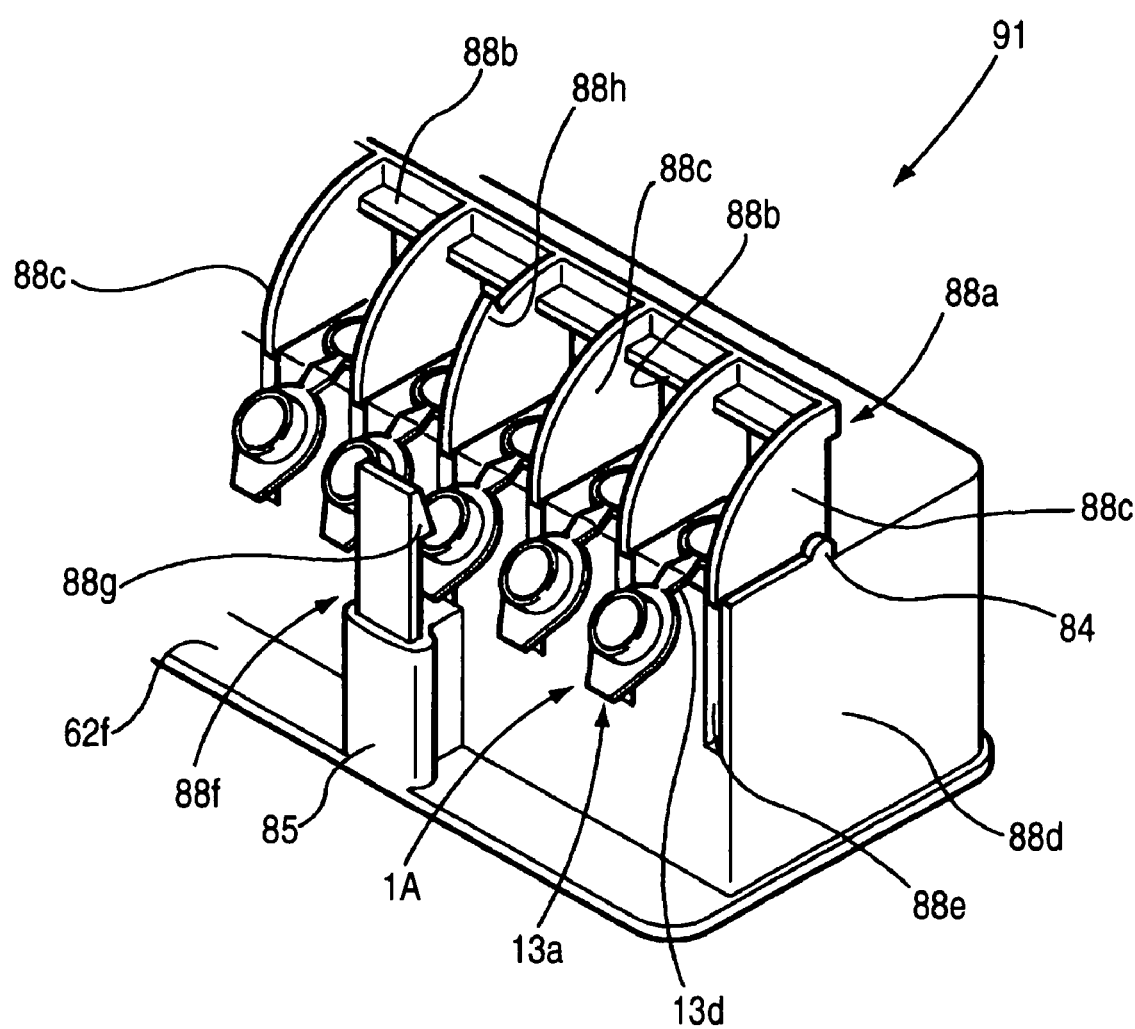
FIG. 26 is a perspective view of an apparatus for inserting and erecting a microtube according to another embodiment.
Figure 27A:
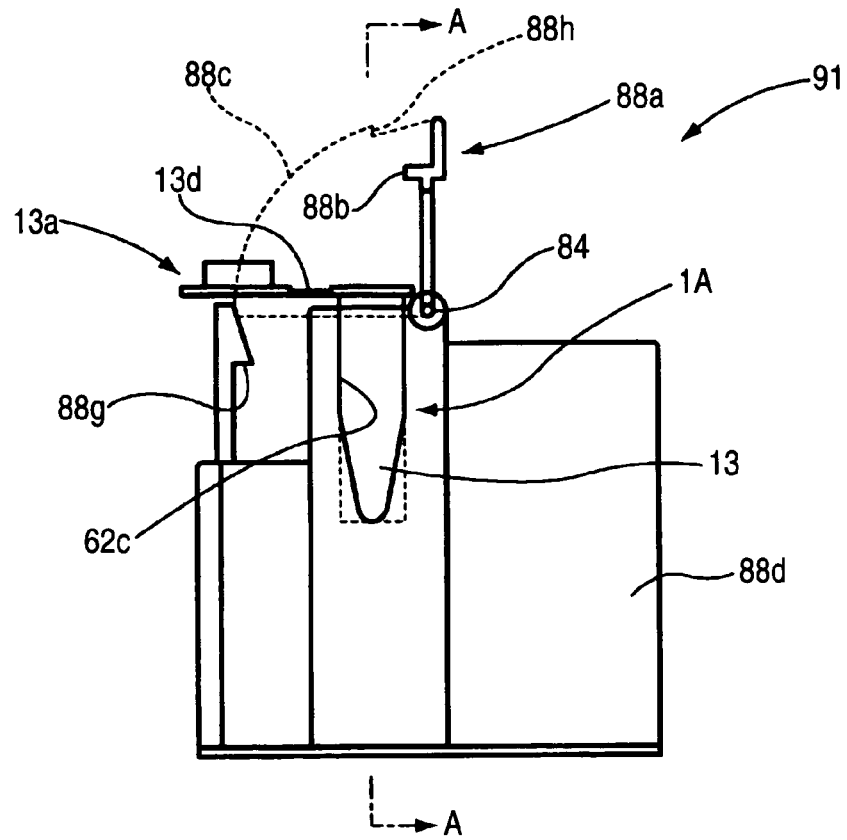
FIG. 27A is an operation explanation view showing a state before hold of the cap portion by the press-bending member.
Figure 27B:
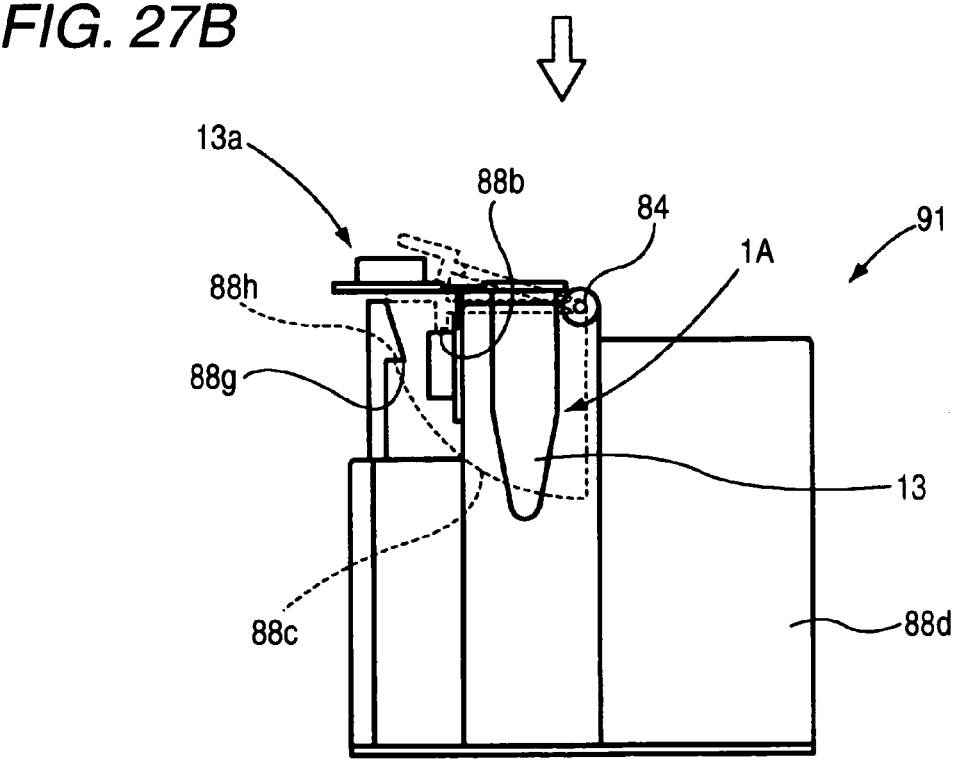
FIG. 27B is an operation explanation view showing a state after the hold of the cap portion by the press-bending member.
Figure 28:
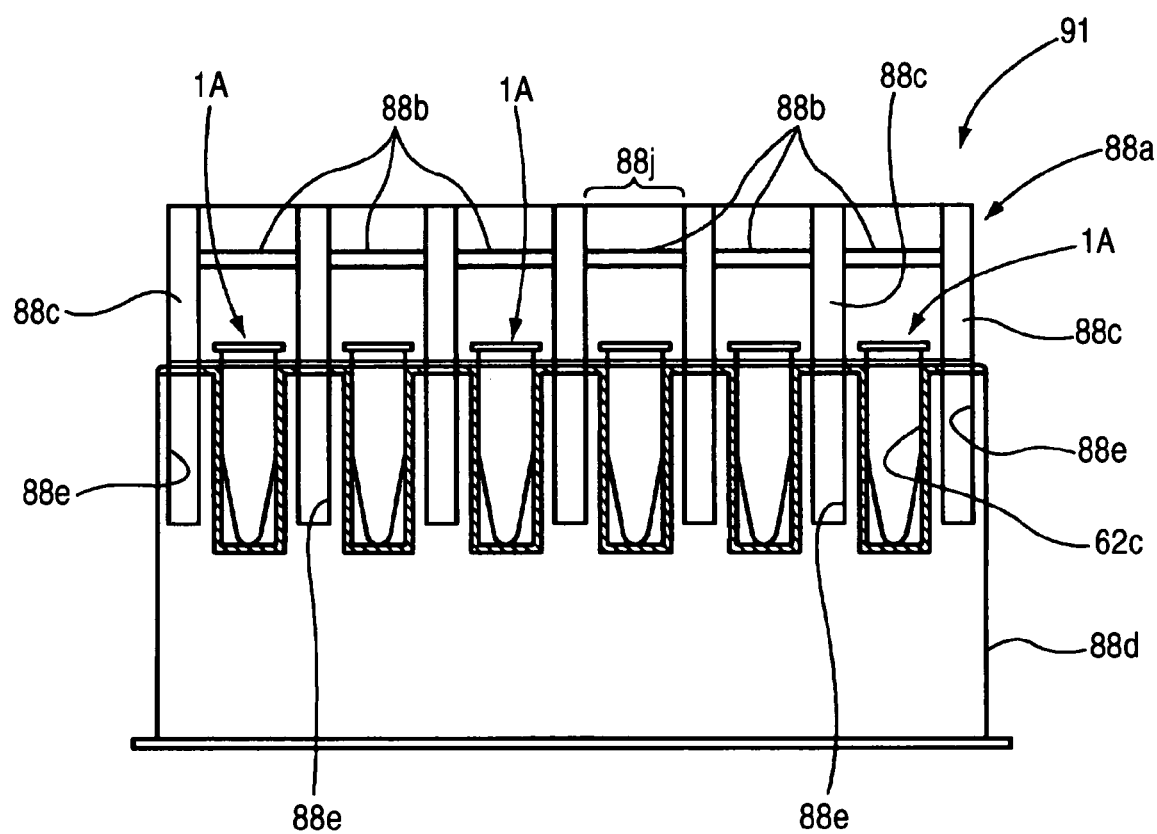
FIG. 28 is a cross sectional view which views A-A line of FIG. 27A in an arrow direction.
Figure 29A:
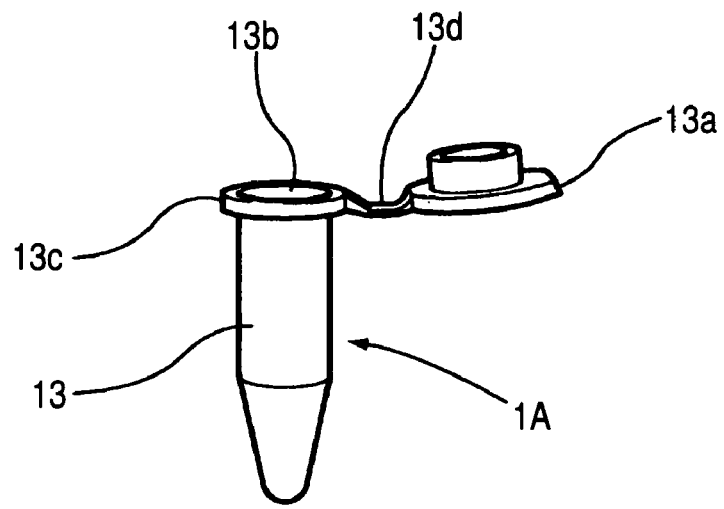
FIG. 29A is an explanation view of a microtube with a cap.
Figure 29B:
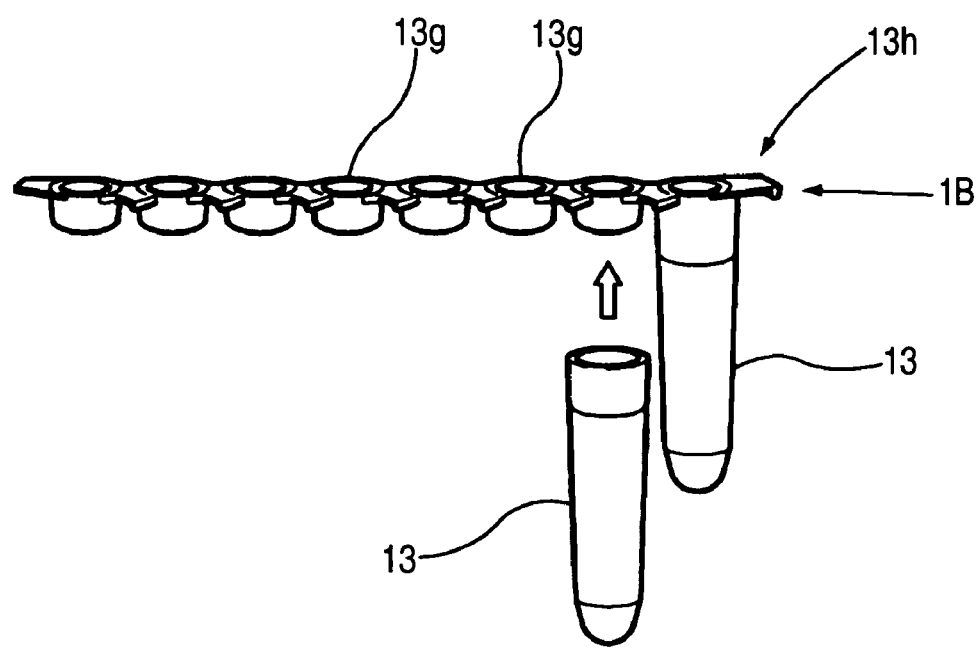
FIG. 29B is an explanation view of a rubber cap type microtube.
Figure 30:
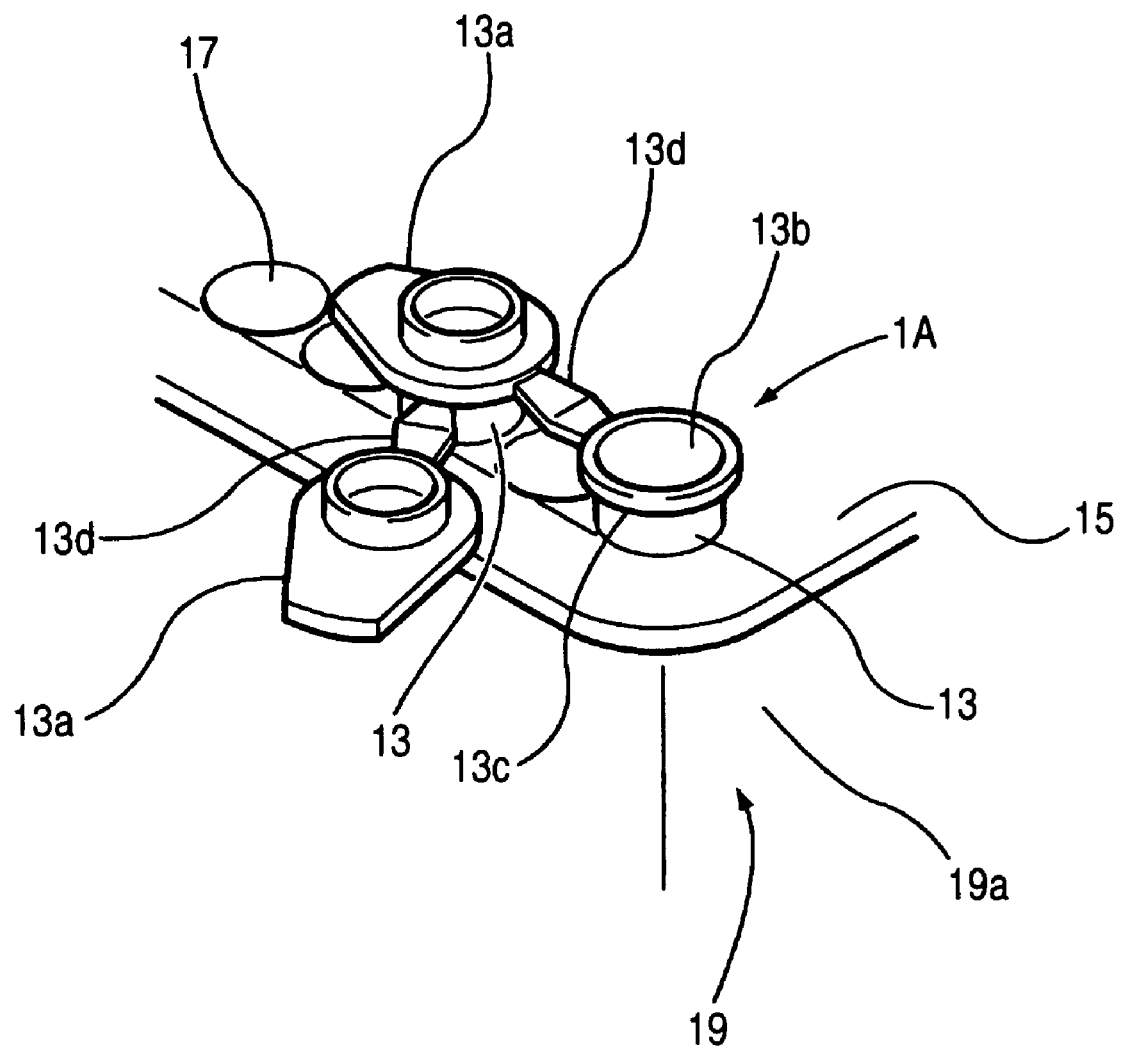
FIG. 30 is a main portion perspective view showing a state that a cap portion of a microtube with a cap closes an opening portion of an adjacent microtube in a conventional apparatus for inserting and erecting a microtube.

FIG. 26 is a perspective view of an apparatus for inserting and erecting a microtube according to another embodiment, FIG. 27A is an operation explanation view showing a state before holding of the cap portion by a press-bending member, FIG. 27B is an operation explanation view showing a state after holding of the cap portion by the press-bending member, and FIG. 28 is a cross sectional view which views A-A line of FIG. 27A in an arrow direction. Moreover, the same symbols are attached to the same members shown in FIG. 23 to FIG. 25, overlapping explanation will be omitted.

In the apparatus for inserting and erecting a microtube 91 of the embodiment, small plate-shaped press-bending pieces 88*b*, which correspond to the hinge portions 13*d* respectively, are arranged at equal intervals on a press-bending member 88*a*. A pair of cap position regulation plates 88*c* having a gap 88*j* (see FIG. 28), into which the cap portion 13*a* can be inserted, is provided on right and left sides of each press-bending piece 88*b*.

In the present embodiment, the cap position regulation plate 88*c* is formed in a fan-shape and is capable of being inserted into a slit 88*e* bored in a casing 88*d*. Further, a locking mechanism 88*f* of the apparatus for inserting and erecting a microtube 91 in the embodiment is constituted by a claw portion 88*g* erecting on the brim portion 62*f*, a lock step portion 88*h* is provided at the cap position regulation plate 88*c* which corresponds to the claw portion 88*g*. The cap position regulation plate 88*c* regulates a position of the cap portion 13*a* in a projection direction from the casing 88*d* while rotating the tube main body 13 in advance of press-bending of the cap portion 13*a* by the press-bending piece 88*b*.

In the apparatus for inserting and erecting a microtube 91, as shown in FIG. 27A, the press-bending member 88*a* is rotated around the shaft 84 to be arranged upward in advance of insertion of the microtube with the cap 1A. The tube main body 13 of the microtube with the cap 1A is inserted into a hole of the casing 88*d* in this state. As shown in FIG. 28, the cap position regulation plates 88*c* are arranged at right and left sides of each microtube with the cap 1A in this state.

Next, when the press-bending member 88*a* is rotated to the front side, the cap position regulation plate 88*c* enters into the slit 88*e* from a rotation tip side in advance of contact of the press-bending piece 88*b* with the hinge portion 13*d*. At this time, if there exists the cap portion 13*a* rotated in a direction of overlapping with the opening portion 13*b* of the adjacent tube main body 13, the microtube with the cap 1A is rotated in a direction that the cap portion 13*a* is housed in the gap 88*j* by being pressured to the cap position regulation plate 88c. Consequently, in the microtube with the cap 1A, just before the press-bending piece 88b comes into contact with the hinge portion 13d, the cap portion 13a is arranged at a rotation position projected on the front side of the casing 88d.

When the press-bending member 88a is further pressed down in this state, as shown in FIG. 27B, in the microtube with the cap 1A, the hinge portion 13d is press-bent downward by the press-bending piece 88b, and the cap portion 13a positioned of the tip of the hinge portion becomes substantially parallel with the front surface of the casing 88d to be press-bent. Further, the claw portion 88g is locked on the lock step portion 88h in this state, so that the press-bending member 88a is locked and held on the casing 88d by the locking mechanism 88f in a state of press-bending the cap portion 13a. The apparatus for inserting and erecting a microtube 91 is set in the apparatus for automatically extracting nucleic acid in this state.

According to the apparatus for inserting and erecting a microtube 91, even though the microtube with the cap 1A inserted and erected into the insertion port 62b of the casing 88d becomes rotated to an optional direction and the cap portion 13a closes the opening portion 13b of the adjacent tube main body 13, owing to rotation of the press-bending member 88a, the pair of cap position regulation plates 88c which are provided on the both sides of the press-bending member 88a respectively, first comes into contact with a side portion of the hinge portion 13d, makes the cap portion 13a project from the casing 88d while rotating the tube main body 13 with the rotation of the press-bending member 88a, thereby allowing the cap portion 13a to be arranged at the gap 88j between the one pair of cap position regulation plates 88c. When the press-bending member 88a is further rotated in this state, it can press-bend and hold the hinge portion 13d downward. Therefore, according to the apparatus for inserting and erecting a microtube 91, owing to the rotation of the press-bending member 88a, it is possible to make all the cap portions 13a turn to the same direction, and to omit a complicated work in which the cap portion 13a is arranged in a fixed direction with fingers before the rotation of the press-bending member 88a.

An apparatus for extracting nucleic acid of the present invention can perform nucleic acid extraction treatment efficiently, easily and quickly, the treatment being excellent in automation properties and having a high reproducibility.

The entire disclosure of each and every foreign patent application from which the benefit of foreign priority has been claimed in the present application is incorporated herein by reference, as if fully set forth.

What is claimed is:

1. An apparatus for extracting nucleic acid, comprising:
    a nucleic acid extraction cartridge equipped with a filter member adapted to adsorb nucleic acid molecules, wherein the cartridge is adapted to be pressurized;
    a first structure adapted to hold the nucleic acid extraction cartridge;
    a waste liquid container;
    a recovering container;
    a second structure adapted to hold the waste liquid container and the recovering container;
    a third structure adapted to hold both the first structure and the second structure;
    a holding mechanism comprising the first structure, the second structure and the third structure;
    an apparatus main body;
    a pressurized air feeding mechanism having a single pressurizing nozzle adapted to introduce a pressurized air into the cartridge through the single pressurizing nozzle;
    a dispensing mechanism having a first dispensing nozzle and a second dispensing nozzle adapted to dispense a washing solution and a recovering solution into the cartridge, respectively; and
    a moving mechanism adapted to relatively move the pressurizing nozzle of the pressurized air feeding mechanism to the holding mechanism,
    wherein the third structure is attachable to and detachable from the apparatus main body,
    wherein the second structure comprises a casing comprising a plurality of insertion ports for a microtube with a cap,
    wherein the plurality of insertion ports are juxtaposed on an upper surface of the casing,
    wherein the apparatus further comprises;
    a press-bending member rotatably supported around an axis of a juxtaposition direction of the plurality of insertion ports provided on the casing, and
    wherein the press-bending member is adapted to hold a cap portion of the microtube with the cap by press-bending the cap portion projected from the casing downward, in the second structure.

2. The apparatus for extracting nucleic acid according to claim 1, further comprising a microtube with a cap, wherein the microtube with the cap comprises:
    a tube main body;
    a flange portion provided on a circumferential edge of a tube opening portion;
    a cap portion;
    a hinge portion that connects the cap portion with the flange portion; and
    a cylinder portion projected on a flange portion close contact surface of the cap portion, and inserted into the tube opening portion, and
    wherein the press-bending member contacts the hinge portion to press-bend and hold the cap portion downward.

3. The apparatus for extracting nucleic acid according to claim 1, further comprising a pair of cap position regulation plates comprising a gap into which the cap portion is insertable, and
    wherein the regulation plates are operably located near the cap portion in a projecting direction from the casing while rotating the tube main body in advance of a press-bending of the cap portion, and is provided at both sides of the press-bending member.

4. The apparatus for extracting nucleic acid according to claim 2, further comprising a locking mechanism positioned over the press-bending member and the case, wherein said locking mechanism releasably holds the press-bending member press-bending the cap portion to the casing is provided over the press-bending member and the casing.

5. The apparatus for extracting nucleic acid according to claim 1, wherein the first and second structures are held by the third structure, and the nucleic acid extraction cartridge held by the first structure is arranged opposite to the waste liquid container held by the second structure, and wherein the third structure comprises at least one insertion passage.

6. The apparatus for extracting nucleic acid according to claim 5, further comprising:
    a movement operation member adapted to move the second structure relative to the first structure such that either the waste liquid container or the recovering container is positioned under the nucleic acid extraction cartridge.

7. The apparatus for extracting nucleic acid according to claim 5,
    wherein a plurality of combinations of the nucleic acid extraction cartridge and the waste liquid container are provided, and wherein a plurality of combinations of the nucleic acid extraction cartridge and the recovering container are provided.

8. The apparatus for extracting nucleic acid according to claim 5, further comprising a pair of gripping members operably positioned on both sides of the third structure.

9. An apparatus for extracting nucleic acid, comprising:
a nucleic acid extraction cartridge equipped with a filter member adapted to adsorb nucleic acid molecules, wherein the cartridge is adapted to be pressurized;
a first structure adapted to hold the nucleic acid extraction cartridge;
a waste liquid container;
a recovering container;
a second structure adapted to hold the waste liquid container and the recovering container;
a third structure adapted to hold both the first structure and the second structure;
a holding mechanism comprising the first structure, the second structure and the third structure;
an apparatus main body;
a pressurized air feeding mechanism having a single pressurizing nozzle adapted to introduce a pressurized air into the cartridge through the single pressurizing nozzle;
a dispensing mechanism having a first dispensing nozzle and a second dispensing nozzle adapted to dispense a washing solution and a recovering solution into the cartridge, respectively; and
a moving mechanism adapted to relatively move the pressurizing nozzle of the pressurized air feeding mechanism to the holding mechanism,
wherein the third structure is attachable to and detachable from the apparatus main body,
wherein the first and second structures are held by the third structure, and the nucleic acid extraction cartridge held by the first structure is arranged opposite to the waste liquid container held by the second structure, and
wherein the third structure comprises at least one insertion passage, and
a concave portion that caves into a rear side from a front side of the apparatus main body at least at the front side of the apparatus main body near an equipped position of the third structure to the apparatus main body in order to ensure side spaces of the third structure.

10. An apparatus for extracting nucleic acid, comprising:
a nucleic acid extraction cartridge equipped with a filter member adapted to adsorb nucleic acid molecules, wherein the cartridge is adapted to be pressurized;
a first structure adapted to hold the nucleic acid extraction cartridge;
a waste liquid container;
a recovering container;
a second structure adapted to hold the waste liquid container and the recovering container;
a third structure adapted to hold both the first structure and the second structure;
a holding mechanism comprising the first structure, the second structure and the third structure;
an apparatus main body;
a pressurized air feeding mechanism having a single pressurizing nozzle adapted to introduce a pressurized air into the cartridge through the single pressurizing nozzle;
a dispensing mechanism having a first dispensing nozzle and a second dispensing nozzle adapted to dispense a washing solution and a recovering solution into the cartridge, respectively; and
a moving mechanism adapted to relatively move the pressurizing nozzle of the pressurized air feeding mechanism to the holding mechanism,
wherein the third structure is attachable to and detachable from the apparatus main body,
wherein the first and second structures are held by the third structure, and the nucleic acid extraction cartridge held by the first structure is arranged opposite to the waste liquid container held by the second structure, and
wherein the third structure comprises at least one insertion passage, and
projections that regulate an insertion direction of the second structure to a specific direction on a way of the insertion passage, through which the second structure is inserted into an inside of the third structure wherein the second structure is operatively associated with the third structure.

11. The apparatus for extracting nucleic acid according to claim 10,
wherein the projections comprise: a first projection projected on one side of an inner side wall of an insertion passage of the third structure; and a second projection projected on an outer side wall surface of the second structure facing an inner side wall of the third structure opposed to the first projection when the second structure is inserted into an inner side of the third structure in the specific direction, and
wherein the first projection and the second projection do not interfere with each other when the second structure is inserted into the specific direction, and the first projection and the second projection interfere with each other so that an insertion operation is regulated when the second structure is inserted into an opposite direction of the specific direction.

12. A method for automated purification of nucleic acids, which comprises:
providing a sample solution containing nucleic acid and containing an impurity;
providing the apparatus for extracting nucleic acid according to claim 1;
pressurizing the nucleic acid extraction cartridge of the apparatus;
injecting the sample solution into the extraction cartridge, wherein the nucleic acid is adsorbed to the filter member;
recovering a discharge from the injected sample into the waste liquid container, wherein the discharge passes through the filter member;
pressurizing a washing solution;
dispensing the pressurized washing solution into the nucleic acid extraction cartridge, wherein the nucleic acid adsorbed to the filter member is not released into the pressurized washing solution, and wherein the impurity is released from the filter member into the washing solution, thereby removing the impurity from the sample;
pressurizing a recovering solution; and
dispensing the pressurized recovering solution into the nucleic acid extraction cartridge, releasing the adsorbed nucleic acid from the filter member into the recovering container, thereby purifying the nucleic acid in the sample.

* * * * *